United States Patent
Srivenugopal et al.

(10) Patent No.: US 11,957,766 B2
(45) Date of Patent: Apr. 16, 2024

(54) HNQO1-ACTIVATABLE FLUORESCENT PROBE FOR IMAGING CANCER CELLS IN-VITRO AND IN-VIVO

(71) Applicant: Texas Tech University System, Lubbock, TX (US)

(72) Inventors: Kalkunte S. Srivenugopal, Amarillo, TX (US); Surendra R. Punganuru, Amarillo, TX (US)

(73) Assignee: TEXAS TECH UNIVERSITY SYSTEM, Lubbock, TX (US)

( * ) Notice: Subject to any disclaimer, the term of this patent is extended or adjusted under 35 U.S.C. 154(b) by 625 days.

(21) Appl. No.: 16/950,107

(22) Filed: Nov. 17, 2020

(65) Prior Publication Data

US 2021/0154330 A1 May 27, 2021

Related U.S. Application Data

(60) Provisional application No. 62/940,606, filed on Nov. 26, 2019.

(51) Int. Cl.
*A61B 5/00* (2006.01)
*A61B 8/00* (2006.01)
*A61B 10/00* (2006.01)
*A61K 49/00* (2006.01)
*C07C 255/38* (2006.01)
*C07C 255/44* (2006.01)
*C12Q 1/32* (2006.01)
*G01N 33/574* (2006.01)
*G01N 33/58* (2006.01)

(52) U.S. Cl.
CPC ........ *A61K 49/0052* (2013.01); *C07C 255/38* (2013.01); *C07C 255/44* (2013.01); *C12Q 1/32* (2013.01); *G01N 33/57496* (2013.01); *G01N 33/582* (2013.01)

(58) Field of Classification Search
CPC ............ A61K 49/0052; A61K 49/0021; C07C 255/38; C07C 255/44; C07C 255/31; C12Q 1/32; G01N 33/57496; G01N 33/582; G01N 33/574; G01N 33/581; G01N 33/533
See application file for complete search history.

(56) References Cited

PUBLICATIONS

Punganuru et al. (Scientific Reports 2019, 9, 8577; p. 1-12 and supplemental materials).*
Punganuru et al. (Cancer Res. 2019, 79, abstract 1948).*
Silvers, W. C. et al. Profluorogenic reductase substrate for rapid, selective, and sensitive visualization and detection of human cancer cells that overexpress NQO1. J. Am. Chem. Soc. 135, 309-314 (2013).
Silvers, W.C. et al. Shedding light by cancer redox—human NAD(P)H: Quinone oxidoreductase 1 activation of a cloaked fluorescent dye. Chem. Commun. 2011, 47, 11264-11266.
Stummer, W. et al. Extent of resection and survival in glioblastoma multiforme: Identification of and adjustment for bias. Neurosurgery 2008, 62, 564-576.
Swanson, K.I. et al. Fluorescent Cancer-Selective Alkylphosphocholine Analogs for Intraoperative Glioma Detection, Neurosurgery 2015, 76, 115-124.
Tonelli, C. et al. Transcriptional Regulation by Nrf2. Antioxid Redox Signal. 2018, 29, 1727-1745.
Winski, S.L. et al. Characterization of a Mechanism Based Inhibitor of NAD(P)H:Quinone Oxidoreductase 1 by Biochemical, X-ray Crystallographic, and Mass Spectrometric Approaches. Biochemistry 2001, 40, 15135-15142.
Wirth, D. et al. Identifying brain neoplasms using dye-enhanced multimodal confocal imaging. J. Biomed Opt. 2012, 17, 026012, doi: 10.1117/1.JBO.17.2.026012.
Yang, Y. et al. Clinical implications of high NQO1 expression in breast cancers. J. Exp. Clin. Cancer Res. 2014, 33, 14, doi: 10.1186/1756-9966-33-14.
Zhang, C. et al. Design and synthesis of near-infrared fluorescence enhancement probes for the cancer-specific enzyme hNQO1. Dyes and Pigm. 2017, 143, 245-251.
Zhang, K. et al. NAD(P)H:Quinone Oxidoreductase 1 (NQO1) as a Therapeutic and Diagnostic Target in Cancer. J. Med. Chem. 2018, 61, 6983-7003.
Zhang, W. et al. Near-infrared fluorescent probe with remarkable large stokes shift and favorable water solubility for real-time tracking leucine aminopeptidase in living cells and in vivo. Anal Chem. 89, 12319-12326 (2017).
Zhang, X. et al. Near-Infrared Molecular Probes for In Vivo Imaging, Curr Protoc Cytom. Apr. 2012 ; Chapter: Unit12.27. doi:10.1002/0471142956.cy1227s60, 28 pages.
Belykh, E. et al. Intraoperative Fluorescence Imaging for Personalized Brain Tumor Resection: Current State and Future Directions. Front. Surg. 2016, 3, 55.
Best, Q.A. et al. Environmentally Robust Rhodamine Reporters for Probe-based Cellular Detection of the Cancer-linked Oxidoreductase hNQO1. ACS Chem. Biol. 2016, 11, 231-240.
Bian, J. et al. Affinity-based small fluorescent probe for NAD(P)H:quinone oxidoreductase 1 (NQO1). Design, synthesis and pharmacological evaluation. Eur. J. Med. Chem. 2017, 127, 828-839.
Cuff, S. et al. An improved cell-permeable fluorogenic substrate as the basis for a highly sensitive test for NAD(P)H quinone oxidoreductase 1 (NQO1) in living cells. Free Radic. Biol. Med. 2018, 116, 141-148.
Cui, X. et al. NAD(P)H: Quinone oxidoreductase-1 overexpression predicts poor prognosis in small cell lung cancer. Oncol. Rep. 2014, 32, 2589-2595.
Dias, G.G. et al. Quinone based fluorophores for imaging biological processes. Chem. Soc. Rev. 2018, 47, 12-27.
Dinkova-Kostova, A.T. et al. NAD(P)H:quinone acceptor oxidoreductase 1 (NQO1), a multifunctional antioxidant enzyme and exceptionally versatile cytoprotector. Arch. Biochem. Biophys. 2010, 501, 116-123.

(Continued)

*Primary Examiner* — Michael G. Hartley
*Assistant Examiner* — Melissa J Perreira
(74) *Attorney, Agent, or Firm* — Edwin S. Flores; Daniel J. Chalker; Chalker Flores, LLP

(57) ABSTRACT

The present invention includes a probe, an assay, a method of detecting, a human NAD(P)H quinone oxidoreductase-1 (hNQO1) enzyme activity with a fluorescent probe comprising a quinone propionic acid (QPA) conjugated to dicyanoisophorone (DCP), wherein the hNQO1 reduces the probe to releases a fluorescent DCP, and a method of making the same.

25 Claims, 9 Drawing Sheets

(56) References Cited

PUBLICATIONS

Dong, Y. et al. Prostate cancer radiosensitization through PARP-1 hyperactivation. Cancer Res. 2010, 70, 8088-8096.

Eranster, L. et al. Soluble diaphorase in animal tissues. Acta Chem. Scand. 1958, 12, 595-602.

Fass, L. Imaging and cancer: a review. Mol. Oncol. 2, 115-152 (2008).

Fei, Q. et al. Rational construction of probes rendering ratiometric response to the cancer-specific enzyme NQO1. Dyes Pigm. 2017, 136, 846-851.

Frangioni, J. V. New technologies for human cancer imaging. J. Clin. Oncol. 26, 4012-4021 (2008).

Gaikwad, A. et al. In vivo role of NAD(P)H: Quinone Oxidoreductase 1 (NQO1) in the regulation of intracellular redox state and accumulation of abdominal adipose tissue. J. Biol. Chem. 276, 22559-22564 (2001).

Garland, M. et al. A bright future for precision medicine: Advances in fluorescent chemical probe design and their clinical application. Cell Chem. Biol. 23, 122-136 (2016).

Gontijo, T.B. et al. Novel fluorescent lapachone based BODIPY: Synthesis, computational and electrochemical aspects, and subcellular localisation of a potent antitumour hybrid quinone. Chem. Commun. 2016, 2, 13281-13284.

Gontijo, T.B. et al. On the synthesis of quinone based BODIPY hybrids: New insights on antitumor activity and mechanism of action in cancer cells. Bioorg. Med. Chem. Lett. 2017, 27, 4446-4456.

Hettiarachchi, S.U. et al. Detection and Cellular Imaging of Human Cancer Enzyme Using a Turn-On, Wavelength-Shiftable, Self-Immolative Profluorophore. J. Am. Chem. Soc. 2014, 136, 7575-7578.

Huang, X. et al. An NQO1 substrate with potent antitumor activity that selectively kills by PARP1-induced programmed necrosis. Cancer Res. 72, 3038-3047 (2012).

Ji, L. et al. Correlation of Nrf2, NQO1, MRP1, cmyc and p53 in colorectal cancer and their relationships to clinicopathologic features and survival. Int. J. Clin. Exp. Pathol. 2014, 7, 1124-1131.

Kellar, A. et al., Preclinical Murine Models for Lung Cancer: Clinical Trial Applications, D. Biomed. Res. Int. 621324 org/10.1155/2015/621324 18 pages (2015).

Kwon, N. et al. An efficient two-photon fluorescent probe for human NAD(P)H:quinone oxidoreductase (hNQO1) detection and imaging in tumor cells. Chem. Commun. 2017, 53, 525-528.

Lacivita, E. et al. Activatable fluorescent probes: A new concept in optical molecular imaging. Curr. Med. Chem. 19, 4731-4741 (2012). [Abstract].

Lee, S. et al. Activatable molecular probes for cancer imaging. Curr. Top. Med. Chem. 2010, 10, 1135-1144.

Leinonen, H.M. et al. Role of the Keap1-Nrf2 pathway in cancer. Adv. Cancer Res. 2014, 122, 281-320.

Lewis, A.M.; Ough, M.; Du, J.; Tsao, M.S.; Oberley, L.W.; Cullen, J.J. Targeting NAD(P)H:Quinone Oxidoreductase (NQO1) in Pancreatic Cancer. Mol. Carcinog. 2017, 56, 1825-1834.

Li, L. S. et al. NQO1-Dependent radiosensitization of head and neck cancer. Mol. Cancer Ther. 15, 1757-1767 (2016).

Li, L.S. et al. NQO1-Mediated Tumor-Selective Lethality and Radiosensitization for Head and Neck Cancer. Mol. Cancer Ther. 2016, 15, 1757-1767.

Li, R. et al. The three dimensional structure of NAD(P)H:quinone reductase, a flavoprotein involved in cancer chemoprotection and chemotherapy: Mechanism of the two-electron reduction. Proc. Natl. Acad. Sci. USA 1995, 92, 8846-8850.

Li, Z. et al. NQO1 protein expression predicts poor prognosis of non-small cell lung cancers. BMC Cancer 2015, 15, 207, doi: 10.1186/s12885-015-1227-8.

Lin, L. et al. Significance of NQO1 overexpression for prognostic evaluation of gastric adenocarcinoma. Exp. Mol. Pathol. 96, 200-205 (2014).

Liu, B. et al. Gastrointestinal imaging-practical magnetic resonance imaging approach. World J. Radiol. 6, 544-566 (2016).

Luo, S. et al. A Probe for the Detection of Hypoxic Cancer Cells. ACS Sens. 2, 1139-1145 (2017).

Luo, S. et al. A review of NIR dyes in cancer targeting and imaging. Biomaterials, 32, 7127-7138 (2011).

Madala, H.R. et al. Brain- and brain tumor-penetrating disulfiram nanoparticles: Sequence of cytotoxic events and efficacy in human glioma cell lines and intracranial xenografts. Oncotarget 2017, 9, 3459-3482.

Mendoza, M. F. et al. Human NAD(P)H:quinone oxidoreductase type I (hNQO1) activation of quinone propionic acid trigger groups. Biochemistry, 51, 8014-8026 (2012).

Nioi, P. et al. Identification of a novel Nrf2-regulated antioxidant response element (ARE) in the mouse NAD(P)H: quinone oxidoreductase 1 gene: Reassessment of the ARE consensus sequence. Biochem. J. 2003, 374, 337-348.

Oh, E. T. et al. Implications of NQO1 in cancer therapy. BMB Rep. 48, 609-617 (2015).

Okamura, T. et al. NADPH/quinone oxidoreductase is a priority target of glioblastoma chemotherapy. Int. J. Oncol. 2000, 16, 295-598.

Okuda, K. et al. 2-Nitroimidazole-Tricarbocyanine Conjugate as a Near-Infrared Fluorescent Probe for in Vivo Imaging of Tumor Hypoxia. Bioconjugate Chem. 23, 324-329 (2012).

Pan, D. et al. A novel two-photon fluorescent probe with a long Stokes shift and a high signal-to background ratio for human NAD(P)H:quinone oxidoreductase 1 (hNQO1) detection and imaging in living cells and tissues. Analyst 2017, 142, 2624-2630.

Parkinson, E. I. et al. Deoxynyboquinones as NQO1-activated cancer therapeutics. Acc. Chem. Res. 48, 2715-2723 (2015).

Prasai, B. et al. Oxidoreductase-Facilitated Visualization and Detection of Human Cancer Cells. Anal. Chem. 2015, 87, 6411-6418.

Prince, A. C. et al. Characterizing the detection threshold for optical imaging in surgical oncology. J. Surg Oncol. 116, 898-906 (2017).

Punganuru, S. R. et al. Cancer-Specific Biomarker hNQO1-Activatable Fluorescent Probe for Imaging Cancer Cells In Vitro and In Vivo. Cancers (Basel) 10, E470 (2018).

Punganuru, S. R. et al. Design and synthesis of a C7-aryl piperlongumine derivative with potent antimicrotubule and mutant p53-reactivating properties. Eur. J. Med. Chem. 107, 233-244 (2016).

Punganuru, S.R. et al. Conception, synthesis, and characterization of a rofecoxib-combretastatin hybrid drug with potent cyclooxygenase-2 (COX-2) inhibiting and microtubule disrupting activities in colon cancer cell culture and kenograft models. Oncotarget 2018, 9, 26109-26129.

Shen, Z. et al. A Near-Infrared, Wavelength-Shiftable, Turn-on Fluorescent Probe for the Detection and Imaging of Cancer Tumor Cells. ACS Chem. Biol. 2017, 12, 1121-1132.

Shin, W.S. et al. Mitochondria-targeted aggregation induced emission theranostics: Crucial importance of in situ activation. Chem. Sci. 2016, 7, 6050-6059.

\* cited by examiner

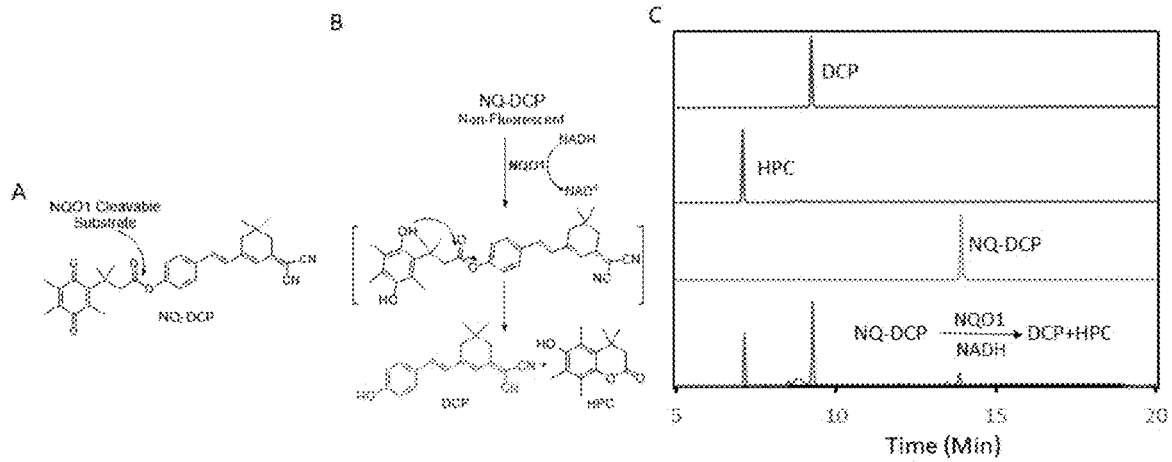
FIG. 1A    FIG. 1B    FIG. 1C
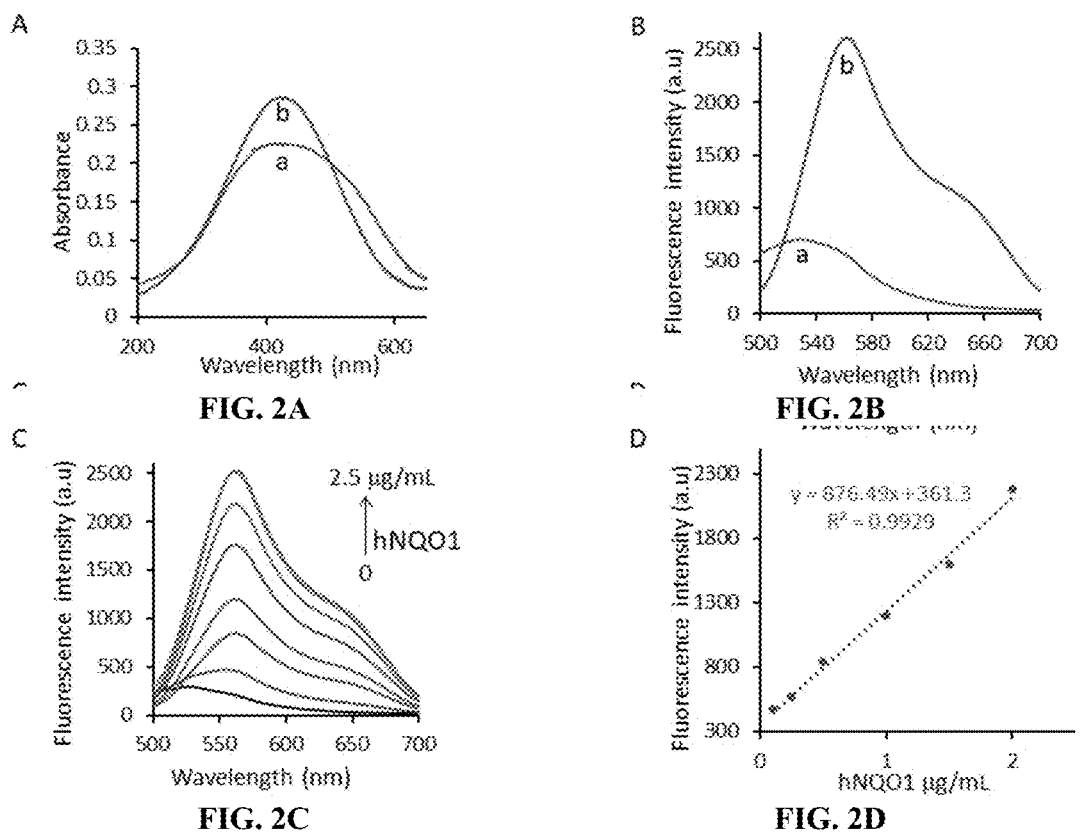
FIG. 2A    FIG. 2B
FIG. 2C    FIG. 2D

FIG. 7C     FIG. 7D

HNQO1-ACTIVATABLE FLUORESCENT PROBE FOR IMAGING CANCER CELLS IN-VITRO AND IN-VIVO

CROSS-REFERENCE TO RELATED APPLICATIONS

This application claims priority to U.S. Provisional Application Ser. No. 62/940,606, filed Nov. 26, 2020, the entire contents of which are incorporated herein by reference.

TECHNICAL FIELD OF THE INVENTION

The present invention relates in general to the field of probes, and more particularly, to novel fluorescent probes for the detection of cancer cells in vitro and in vivo.

STATEMENT OF FEDERALLY FUNDED RESEARCH

None.

BACKGROUND OF THE INVENTION

Without limiting the scope of the invention, its background is described in connection with cancer.

Human NAD(P)H quinone oxidoreductase-1 (hNQO1), formerly referred to as DT diaphorase, is a cytosolic flavoenzyme that plays an essential role in cellular protection against endogenous quinones (e.g., the vitamin E α-tocopherol quinone, menadione, benzene quinones) [1]. It is a homodimer which binds quinones with the co-factor NADH or NADPH, leading to a reduction of the quinones in a two-electron transfer reaction [2]. In addition to its enzymatic activity, NQO1 has been found to be involved in other biological processes such as antioxidant activity and the stabilization of essential regulatory proteins under stress [3]. The enzyme hNQO1 is constitutively expressed at relatively low levels in various normal tissues but is frequently expressed at high levels in most solid tumors such as breast [4], lung [5,6], prostate [7], stomach [8], colon [9], pancreatic [10], brain [11], head, and neck cancer [12]. NQO1 is expressed in many human solid tumors at levels of 200-fold above that in normal tissue and its elevated activity has been closely associated with tumor progression, aggressiveness, resistance to chemotherapy, and poor prognosis [4-12]. As such, hNQO1 has been recognized as a potential biomarker of human malignancies.

The reasons for NQO1 overexpression in cancers are still unclear, however, the elevated oxidative stress prevalent in most malignancies appears to be a link [14]. Like many phase 2 metabolic enzymes inducible by redox stress, the 5' upstream region of the NQO1 gene harbors typical antioxidant response elements (AREs) [15] that associate with the NRF2 (Nuclear factor erythroid-derived 2-like 2) transcription factor, which in turn is stabilized through dissociation from Keap-1 in oxidative milieu [16].

In common with other malignancies that possess higher levels of oxidative stress, the malignant gliomas constitute a highly invasive, heterogeneous, complex, and fatal tumor type, the extent of which is not precisely identifiable by modern imaging techniques [17]. Despite all the current treatment modalities for malignant gliomas, surgical resection is associated with a moderate recurrence-free survival of patients [18]. Therefore, maximal removal of the tumor mass is the primary goal in the treatment of this tumor type. However, the ability of the unaided human eye to detect accurate boarders between cancer and normal tissues during surgery is limited. Recently, fluorescence molecular imaging has emerged as an important aid to assist the optically guided surgery because of its high sensitivity and non-radiation application [19,20]. Particularly, enzyme activated turn-on fluorescent probes hold great promise in accelerating clinical translation by significantly improving the target to background ratio (TBR) and, in turn, the sensitivity and contrast of fluorescence imaging [21,22]. In this context, it is necessary to identify a cancer-specific trait, a biomarker that is stable, dependable and not significantly shared with normal cells.

Previously, hNQO1 activated fluorescent probes were developed based on its property of quinone bio-reduction [23], where the fluorescent probe conjugated with a quinone-based NQO1 substrate as a trigger group, which holds the fluorophore in a quenched state (Table 1). Intense fluorescence of these probes occurs upon specific activation of the quinone moiety by hNQO1. The "trimethyl lock" containing quinone propionic acid (QPA) has been extensively used as an hNQO1-responsive trigger group because of its rapid and selective reduction by hNQO1 to afford hydroquinone analog, which underwent lactonization to release fluorescent probe. Consequently, McCarley group and others have developed several QPA-based fluorescent probes for detection and imaging of hNQO1 in cancer cells. The fluorophores used in these studies include rhodamines [24,25], napthalimides [26-28], Acedan [29], coumarin [30], HO-BODIPY [31], tetraphenylethane [32], amino-acetyl-naphthalene [33], carbocyanines [34-36]. On the other hand, several affinity-based small molecule probes were also developed by linking the hNQO1 inhibitor as the recognition group [37,38]. Although these fluorescent probes have shown good selectivity even in the presence of other cellular reductants, their in vivo applications have been limited.

TABLE 1

Fluorescent probes previously described for the human NAD(P)H quinone oxidoreductase-1 (hNQO1) detection and their comparison with new dicyanoisophorone (DCP) based fluorescent probe (NQ-DCP).

| Fluorescent Probes for hNQO1 (Ref.) | $\lambda_{abs/em}$ (Stokes-Shift) | Application |
|---|---|---|
| [25] | 485/520 (35) | In vitro |
| [26] | 585/624 (39) | in vitro |
| [28] | 374/490 (116) | In vitro |

TABLE 1-continued

Fluorescent probes previously described for the human NAD(P)H quinone oxidoreductase-1 (hNQO1) detection and their comparison with new dicyanoisophorone (DCP) based fluorescent probe (NQ-DCP).

| Fluorescent Probes for hNQO1 (Ref.) | $\lambda_{abs/em}$ (Stokes-Shift) | Application |
|---|---|---|
| [35] | 670/710 (40) | In vitro and in vivo |
| [27] | 440/525 (85) | In vitro |
| [35] | 730/800 (70) | In vitro and in vivo |

TABLE 1-continued

Fluorescent probes previously described for the human NAD(P)H quinone oxidoreductase-1 (hNQO1) detection and their comparison with new dicyanoisophorone (DCP) based fluorescent probe (NQ-DCP).

| Fluorescent Probes for hNQO1 (Ref.) | $\lambda_{abs/em}$ (Stokes-Shift) | Application |
|---|---|---|
| [31] | 509/542 (33) | In vitro |
| [34] | 786/798 (12) | In vitro and in vivo |
| [30] | 360/450 (90) | In vitro |

Thus, while Human NAD(P)H quinone oxidoreductase-1 (hNQO1) has been recognized as an important cancer-related biomarker, with significant overexpression in malignant cells, a need remains to overcome the problems with probes of the prior art that fail to weak signal-to-noise ratios, are unable to enter a cell or are not biocompatible, fail to have a sufficient stokes shift, and/or are limited to in vitro use only. What is needed is the development of an effective probe and method for detecting NQO1 activity with high sensitivity and selectivity in tumors for cancer diagnosis, treatment, and management.

SUMMARY OF THE INVENTION

In one embodiment, the present invention includes an assay to detect human NAD(P)H quinone oxidoreductase-1 (hNQO1) enzyme activity comprising: contacting an hNQO1 enzyme with a probe comprising a quinone propionic acid (QPA) conjugated to dicyanoisophorone (DCP), wherein the hNQO1 reduces the probe releases a fluorescent DCP. In one aspect, the probe is defined as further comprising an ester or amide bond between the QPA and the DCP. In another aspect, the probe has at least one of: a large stokes shift, a high sensitivity and selectivity against hNQO1, a low cytotoxicity, or cell permeability. In another aspect, the probe has the formula:

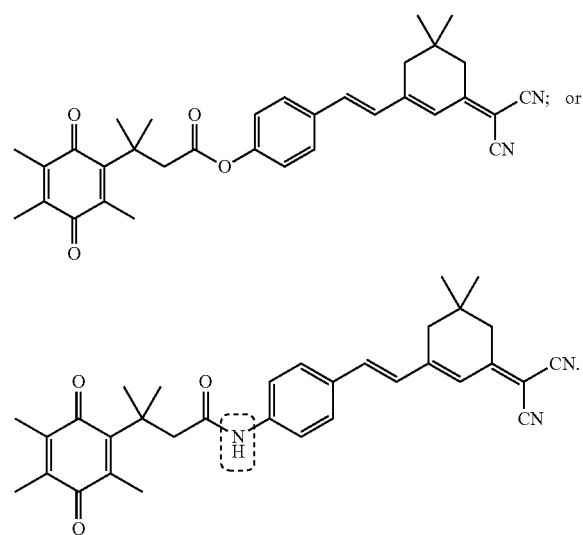 [SMILES: CC1=C(C)C(=O)C(C(C)(C)CC(=O)Oc2ccc(/C=C/C3=CC(=C(C#N)C#N)CC(C)(C)C3)cc2)=C(C)C1=O ; CC1=C(C)C(=O)C(C(C)(C)CC(=O)Nc2ccc(/C=C/C3=CC(=C(C#N)C#N)CC(C)(C)C3)cc2)=C(C)C1=O]

In another aspect, a redox activity of hNQO1 reduces a quinone moiety of QPA into an o-hydroxydihydrocinnamic acid derivative that undergoes lactonization under physiological conditions to yield dihydrocoumarin and fluorescent DCP. In another aspect, the hNQO1 enzyme is in a cell, a tissue, an organ, or a cancer. In another aspect, the hNQO1 enzyme is in a breast, lung, prostate, stomach, colon, pancreatic, brain, or head and neck cancer.

In another embodiment, the present invention includes a probe comprising a quinone propionic acid (QPA) conjugated to a dicyanoisophorone (DCP). In one aspect, the quinone propionic acid (QPA) is conjugated to the dicyanoisophorone (DCP) by an ester or amide bond. In another aspect, the probe has the formula:

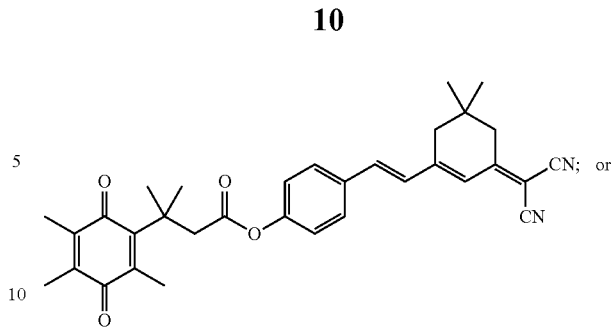

In another aspect, the probe has at least one of: a large stokes shift, a high sensitivity and selectivity against hNQO1, a low cytotoxicity, or cell permeability. In another aspect, the probe is reduced by a human NAD(P)H quinone oxidoreductase-1 (hNQO1) enzyme. In another aspect, the probe is a dicyanoisophorone (ASM) fluorophore conjugated to a NQO1 substrate quinone propionic acid (QPA). In another aspect, a redox activity of hNQO1 reduces a quinone moiety of QPA into an o-hydroxydihydrocinnamic acid derivative that undergoes lactonization under physiological conditions to yield dihydrocoumarin and fluorescent DCP. In another aspect, the hNQO1 enzyme is in a cell, a tissue, an organ, or a cancer. In another aspect, the hNQO1 enzyme is in a breast, lung, prostate, stomach, colon, pancreatic, brain, or head and neck cancer.

In another embodiment, the present invention includes a method of detecting a cancer cell that expresses a human NAD(P)H quinone oxidoreductase-1 (hNQO1) enzyme comprising: contacting the cancer cell with a probe comprising a quinone propionic acid (QPA) conjugated to dicyanoisophorone (DCP), wherein the hNQO1 reduces the probe releases a fluorescent DCP. In one aspect, the quinone propionic acid (QPA) is conjugated to the dicyanoisophorone (DCP) by an ester or amide bond. In another aspect, the quinone propionic acid (QPA) conjugated to dicyanoisophorone (DCP) has the formula:

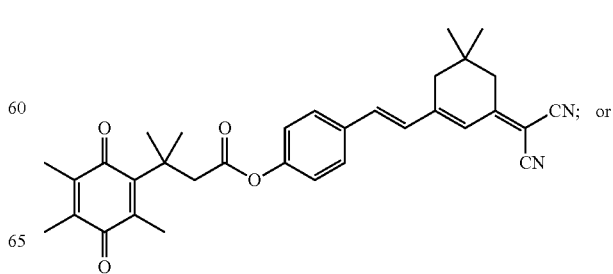

-continued

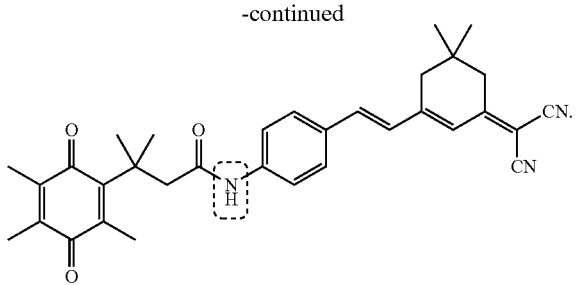

In another aspect, the probe has at least one of: a large stokes shift, a high sensitivity and selectivity against hNQO1, a low cytotoxicity, or cell permeability. In another aspect, a redox activity of hNQO1 reduces a quinone moiety of QPA into an o-hydroxydihydrocinnamic acid derivative that undergoes lactonization under physiological conditions to yield dihydrocoumarin and fluorescent DCP. In another aspect, the hNQO1 enzyme is in a cell, a tissue, an organ, or a cancer. In another aspect, the fluorescence is detected in vivo. In another aspect, the method further comprises the step of obtaining a sample from a subject and measuring the activity of the hNQO1 in the sample. In another aspect, the cancer is a breast, lung, prostate, stomach, colon, pancreatic, brain, or head and neck cancer.

In another embodiment, the present invention includes a method of making a probe comprising a quinone propionic acid (QPA) conjugated to dicyanoisophorone (DCP) comprising:

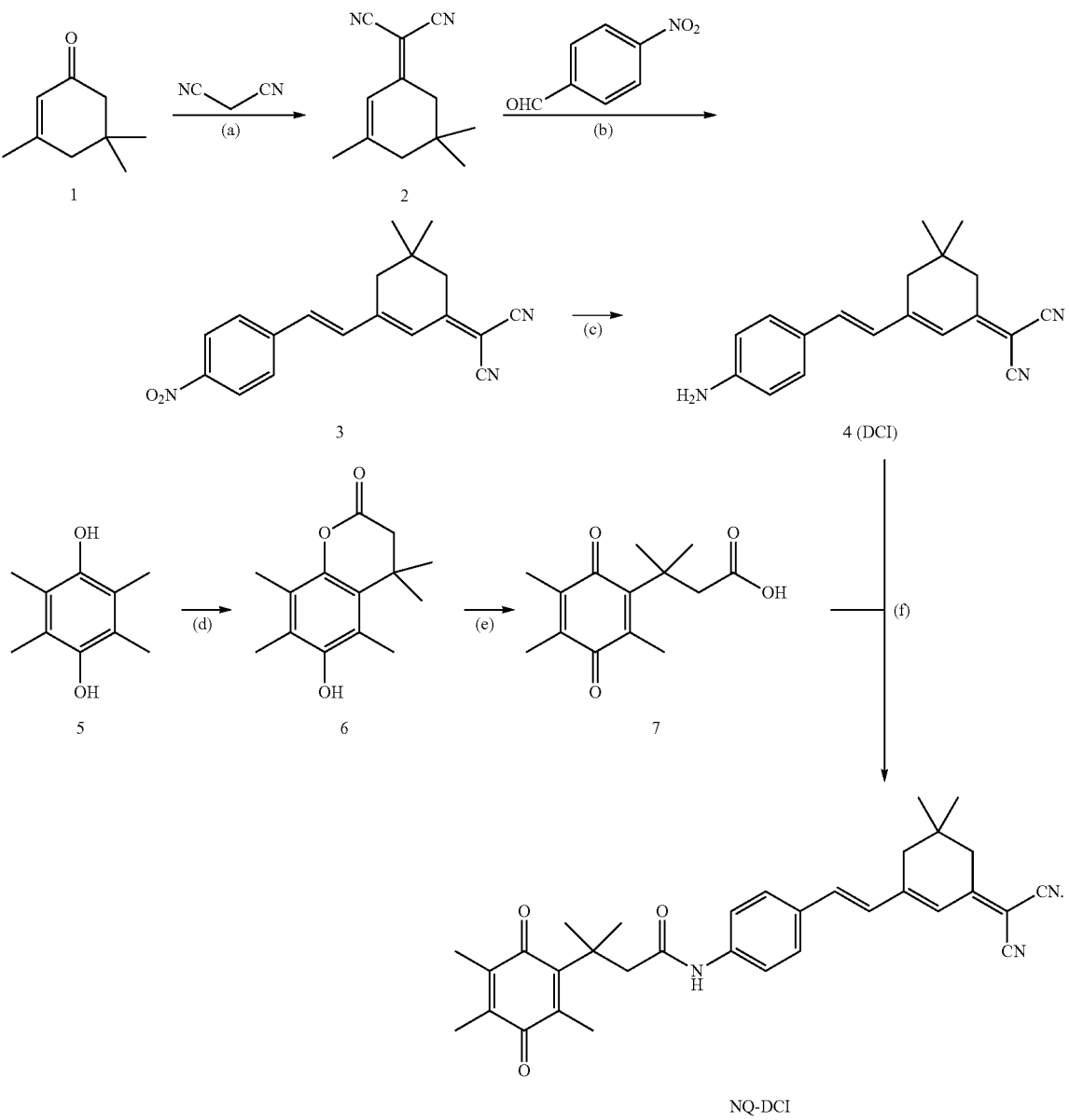

BRIEF DESCRIPTION OF THE DRAWINGS

For a more complete understanding of the features and advantages of the present invention, reference is now made to the detailed description of the invention along with the accompanying figures and in which:

FIGS. 1A to 1C. The NQ-DCP probe is specifically activated by NAD(P)H quinone oxidoreductase-1 (NQO1). (1A) structure of NQ-DCP. (1B) Mechanism of activation of non-fluorescent NQ-DCP in the presence of NADH/NQO1 and release of highly fluorescent dicyanoisophorone (DCP) (1C) high-performance liquid chromatography (HPLC) analysis of NQ-DCP activation. HPLC spectra of NQ-DCP, DCP, dihydrocoumarin (HPC) and the HPLC spectrum of a reaction mixture containing 10 µM NQ-DCP, 2.5 µg/mL NQO1 and 100 µM NADH are shown.

FIGS. 2A to 2D. Changes in absorbance (2A) and fluorescence (2B) of NQ-DCP before (a) and after (b) activation by 2.5 µg/mL of hNQO1 in PBS with 0.1% BSA (pH 7.4). (2C) Fluorescence response of NQ-DCP to different concentrations (0.12, 0.25, 0.5, 1.0, 1.5, 2.0 and 2.5 µg/mL) of hNQO1 in the presence of 100 µM NADH. (2D) The linear fitting curve of fluorescence intensity towards the concentrations of hNQO1 from 0.12 to 2.5 µg/mL, $\lambda_{ex/em}$=420/565 nm.

FIGS. 7A to 7D. (7A) In vivo real-time fluorescence imaging of endogenous NQO1 in subcutaneous U87MG tumor-bearing nude mice after intravenous administration of NQ-DCP (10 mg/kg, 50 µL). (7B) Fluorescence imaging of ex vivo dissected organs namely, the spleen (Sp), Pancreas (Pa), Lungs (Lu), Brain (Br), Heart (H), Kidneys (Ki), and Liver (Li), along with tumor (Tu) after administration NQ-DCP at 30 min. (7C) Luciferase-expressing U87MG cells were injected into the brains of NOD CRISPR Prkdc Il2r gamma (NCG) triple-Immunodeficient mice as described in materials and methods. Representative images of healthy and brain tumor-bearing mice after bioluminescence acquisition following luciferin administration. These images were acquired 15 days after intracranial implantation of U87MG cells. Images were acquired by setting the exposure time to 'auto' to limit the likelihood of an under or over-exposed image. The Living Image software program was used to analyze the tumors by drawing a region of interest (ROI) around each tumor in each image acquired during the bioluminescent imaging session. (7D) Ex-vivo fluorescence imaging of healthy and tumor holding brain from mice after intracranial injection of NQ-DCP using excitation/emission filters 500/580. The scale indicates radiant efficiency.

DETAILED DESCRIPTION OF THE INVENTION

Figure 3A:
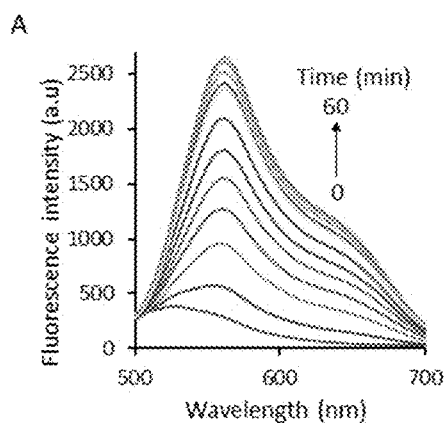
FIGS. 3A to 3E. (3A) Fluorescence spectrum of 10 µM NQ-DCP during a period of 60 min in the presence of 2.5 µg/mL of NQO1 and 100 µM of NADH. (3B) Time-dependent fluorescent intensity changes for the probe NQ-DCI with different concentrations of NQO1 (0 to 25 µM) in PBS with 0.1% BSA (pH 7.4) at $\lambda_{ex/em}$=460/646 nm. (3C) Fluorescence response of NQ-DCP probe (10 µM) to various biologically relevant molecules/enzymes such as the GSH, ALDH, GGT, NTR, GPx, APE1, CBS, CTSL, NADH, GSTpi, NTR+NADH, NQO1, NQO1+NADH, in PBS containing 0.1% BSA (pH 7.4). Bars represent the average final fluorescence intensity at 565 nm after 30 min incubation in three independent experiments (3D). (3E) Inhibitory effect of ES936 on hNQO1 activation of NQ-DCP at different concentrations. The bar diagram represents mean fluorescence intensities (a.u.) ±SEM of NQ-DCP at 565 nm in the presence of different concentrations of ES936 ($\lambda_{ex/em}$=420/565 nm).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present inventors have developed novel fluorescent probes with a large Stokes shift that is essential for biological applications that minimize the interference between the excitation source and the fluorescent emission along with the high target-to-background ratio. With these points in consideration, the fluorescent probe designed herein can be used for endogenous NQO1 imaging using a rationally developed fluorescence probe NQ-DCP with large Stokes shift. NQ-DCP displayed high sensitivity and selectivity against hNQO1 with excellent features such as low cytotoxicity, cell permeability and high target to background ratio in bioimaging NQO1 activity in tumors.

| Fluorescent Probes for hNQO1 (Ref.) | $\lambda_{abs/em}$ (Stokes-Shift) | Application |
|---|---|---|
| Present invention | 420/465 (145) | In vitro and in vivo |

Example 1—Design of the hNQO1 Responsive Fluorescent Probe

In this example, In the present study, a new dicyanoisophorone (DCP) based fluorescent probe (NQ-DCP) is taught that is capable of monitoring hNQO1 activity in vitro and in vivo in both ratiometric and turn-on model. The novel NQ-DCP was prepared by conjugating dicyanoisophorone fluoroprobe with hNQO1 activatable quinone propionic acid (QPA), which remain non-fluorescent until activation by tumor-specific hNQO1. NQ-DCP featured a large Stokes shift (145 nm), excellent biocompatibility, cell permeability, and selectivity towards hNQO1 allowed to differentiate cancer cells from healthy cells. In this example, the novel NQ-DCP was successfully employed NQ-DCP to monitor non-invasive endogenous hNQO1 activity in brain tumor cells in vitro and in xenografted tumors developed in nude mice.

A fluorogenic enzyme substrate probe NQ-DCP (FIG. 1A) was rationally designed based on the "quinone trimethyl lock system" in which QPA is attached to a fluorophore dicyanoisophorone (DCP) via an ester bond. The synthesis of NQ-DCP was started from the preparation of the DCP according to the procedure outlined in Scheme 51 in the Supporting Information. The chemical structures of these compounds were characterized by $^1$H NMR, $^{13}$C NMR, and mass spectrometry. The ester bond with QPA reversibly quenches the fluorescence of the DCP; Upon redox 'activation' by hNQO1, the quinone moiety is reduced to its corresponding o-hydroxydihydrocinnamic acid derivative that undergoes rapid lactonization under physiological conditions to yield dihydrocoumarin, 6-hydroxy-4,4,5,7,8-pentamethylchroman-2-one (HPC) along with a highly fluorescent DCP (FIG. 1B). Activation of NQ-DCP in the presence of hNQO1 was monitored using HPLC analysis by incubating 10 μM NQ-DCP with purified hNQO1 (2.5 μg/mL) in the presence of 100 μM NADH for 30 min. The results indicated that reaction product exhibited chromatographic peaks at 9.2 min and 7.1 min, which matched perfectly with the DCP and HPC indicating the removal of QPA from the NQ-DCP. A weak peak was also observed at 13.8 min, corresponding to the unreacted NQ-DCP probe.

Figure 3B:
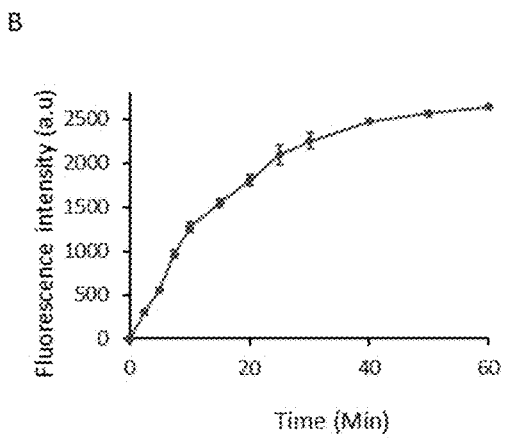

Spectroscopic Response of NQ-DCP to hNQO1. The spectroscopic response of the NQ-DCP probe to an hNQO1 enzyme in the presence of NADH was evaluated in a physiologically relevant buffer (0.1% BSA and 100 μM NADH containing PBS) to determine its ability to detect hNQO1. The absorption and fluorescence spectra of NQ-DCP in the absence and presence of hNQO1 are shown in FIGS. 2A and B. In the presence of hNQO1, although there was a distinct color change from yellow to red there was no difference found in the absorption maximum (425 nm) of NQ-DCP (FIG. 1A). Further, the reaction of NQ-DCP probe with hNQO1 produced a huge fluorescence enhancement at 565 nm with a large Stokes shift (140 nm) (FIG. 2B), which is favorable for sensitive detection and bioimaging analysis, because of a non-overlapping fluorescence emission. Having demonstrated the response of NQ-DCP towards hNQO1, the inventors then investigated its sensitivity for hNQO1 under optimal enzyme reaction conditions. The inventors measured the fluorescence spectra of NQ-DCP (10 μm) following incubation with different concentrations of hNQO1 (0.12, 0.25, 0.5, 1.0, 1.5, 2.0, and 2.5 μg/mL (0.0038, 0.008, 0.016, 0.032, 0.048, 0.064, 0.08 μmol)) along with 100 μM NADH at pH 7.4 for 30 min. As shown in FIG. 2C, in the absence of hNQO1, NQ-DCP was highly stable, with little or no fluorescence enhancement after 30 min. On incubation with hNQO1, the fluorescence intensity at 565 nm increased progressively with the NQO1 concentration and reached a maximum when the hNQO1 concentration was 2.5 μg/mL. The fluorescence intensity at 565 nm was linear with hNQO1 concentration, 0.25-2.0 μg/mL (FIG. 2D). The hNQO1 detection limit (LOD) of NQ-DCP was calculated to be as low as 0.095 μg/mL, based on the standard deviation of the response (Sy) and the slope of the calibration curve (S) according to the formula: LOD=3.3(Sy/S). Additionally, the fluorescence spectra showed a time-dependent trend (FIG. 3A), with the emission peak at 565 nm increasing over time and reaching a maximum after 60 min (FIG. 3B).

Figure 3C:
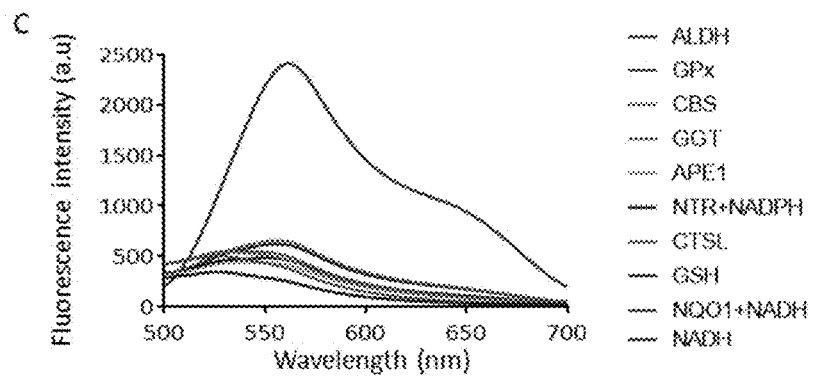
Figure 3D:
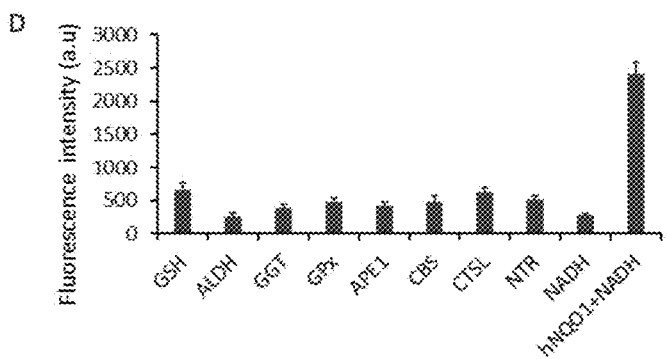
Figure 3E:
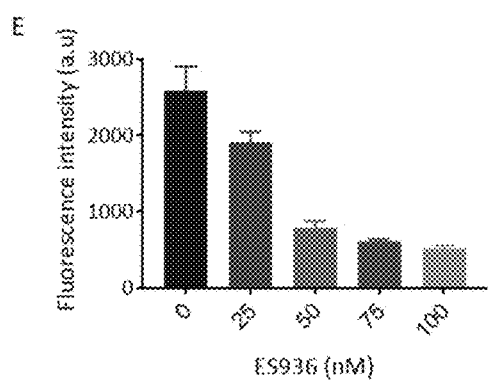

Selectivity of NQ-DCP Towards hNQO1. The specificity of NQ-DCP probe towards hNQO1 was studied by determining its reactivity towards various biomolecules such as the glutathione (GSH, 1 mM), aldehyde dehydrogenase 1 (ALDH1A1, 2.5 μg/mL), gamma-glutamyl transferase (GGT, 10 U), glutathione Peroxidase (GPx, 10 U), apurinic/apyrimidinic endonuclease (APE1, 10 U), cystathionine-β-synthase (CBS, 2 μg/mL), cathepsin L (CTSL, 2 μg/mL), glutathione S-transferase (GST-pi, 2 μg/mL), nitroreductase (NTR, 2 μg/mL) and NADH (100 μM) alone or the combination of and NQO1 (2.5 μg/mL). As shown in FIGS. 3C and D, NQ-DCP demonstrated a high selectivity for hNQO1 over the other enzymes/substrates tested. To gain more insight into the specificity of the probe towards hNQO1, the enzyme was pre-treated with ES936 (0-100 nM), a well-known hNQO1 inhibitor [39] and then incubated with NQ-DCP. As shown in FIG. 3E, ES936 effectively suppressed the fluorescence response in a concentration-dependent manner, indicating the hNQO1-dependent fluorescence response.

Figure 4A:
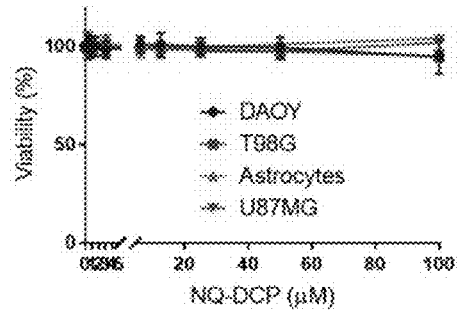
FIGS. 4A to 4C. Comparison of NQO1 activity in human cancer cells (DAOY, T98G, U87MG) and normal cells (astrocytes) in response to NQO1 activated NQ-DCP probe. (4A) Cytotoxicity of NQ-DCP against cancer cells (DAOY, T98G, and U87MG) and normal cells (astrocytes). Cell growth inhibition was analyzed by resazurin reduction assay. Cells were treated with 10 different dilutions of the NQ-DCP (100 µM to 0.196 µM) for 72 h. (4B) Fluorescence images of NQO1-positive cancer cells and NQO1-negative normal cells after incubation of 10 µM NQ-DCP for 1 h. (4C) Western blot showing the expression of NQO1 in cancer cells in comparison to the normal cells; β-actin served as a loading control.

Visualization of Cancer Cells by Fluorescence Imaging of hNQO1. Fluorescence microscopy was used to demonstrate the potential of NQ-DCP fluorescent probe in the visualization of NQO1 in human cancer cells. The cytotoxicity of NQ-DCP was initially evaluated in cultured brain tumor (DAOY, T98G, and U87MG) and normal (astrocytes) cells to assess its biocompatibility using the resazurin reduction assay [40]. The results revealed that NQ-DCP was nontoxic to both normal and cancer cells even at 100 μM after 72 h incubation (FIG. 4A). With excellent biocompatibility demonstrated by the NQ-DCP, the inventors investigated its performance in both cancers (DAOY, T98G, U87MG) and normal (astrocytes) cells. Cells were incubated with NQ-DCP (10 μM) for 60 min, washed with PBS and were imaged under a fluorescence microscope. The results are presented in FIG. 4B. DAOY, T98G, and U87MG cells elicited bright fluorescence signals, whereas the normal cells failed to do so. The presence of hNQO1 protein in cancer cells and its absence in normal cells as determined by western blot analysis confirmed the probe reactivity in cells (FIG. 4C), thereby indicating a good cell permeability of the NQ-DCP and its reaction with the intracellular hNQO1.

Applicability of NQ-DCP for Flow Cytometry. Flow cytometry assays were used to assess the applicability of the NQ-DCP probe to rapidly detect and quantify tumor cells containing hNQO1. The probe was incubated with cell suspensions (DAOY and T98G) for 30 min and a flowcytometry was used to measure the fluorescence ($\lambda_{em}$=586/40) in about 1×10$^4$ individual cells. The resulting histograms and mean fluorescence intensities for both DAOY and T98G cell lines are shown in FIG. 5. A high-intensity unimodal distribution of signal was obtained for NQ-DCP activation in both NQO1-positive cancer cell lines. These results clearly demonstrated that NQ-DCP can quantitatively detect endogenous NQO1 and can be used to rapidly differentiate tumor cells in fluidic streams.

Figure 6A:
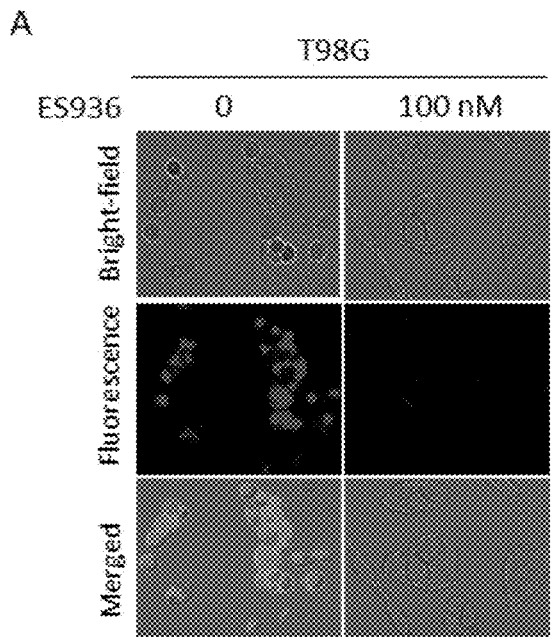
FIGS. 6A and 6B. (6A) Inhibitory effects of NQO1 inhibitor ES936 (100 nM) on NQ-DCI fluorescence. Fluorescence microscopy analysis of T98G cells after treating with NQ-DCP (10 µM) for 1 h in the presence and absence of ES936 (100 nM). (6B) The effect of small interfering RNA (siRNA) knockdown of NQO1 on the activation of NQ-DCP in T98G cells.
Figure 6B:
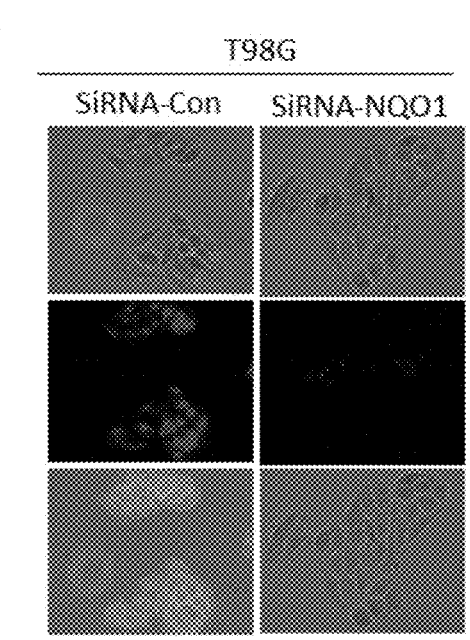

Evaluation of Specificity in Cancer Cells. To show the substrate selectivity of NQ-DCP for hNQO1, T98G cells were pretreated with 100 nM of NQO1 inhibitor ES936 for 6 h and incubated 10 µM of NQ-DCP. As shown in FIG. 6A, ES936 completely blocked the NQ-DCP fluorescence when compared to the untreated cells. In addition, small interfering RNA (siRNA) silencing of the hNQO1 gene induced a decrease in fluorescence ranging from 90-95% compared with a siRNA control after incubation with 10 µM ND-DCP, suggesting that hNQO1 was responsible for the activation NQ-DCP to generate DCP with high fluorescence intensity (FIG. 6B).

Figure 7A:
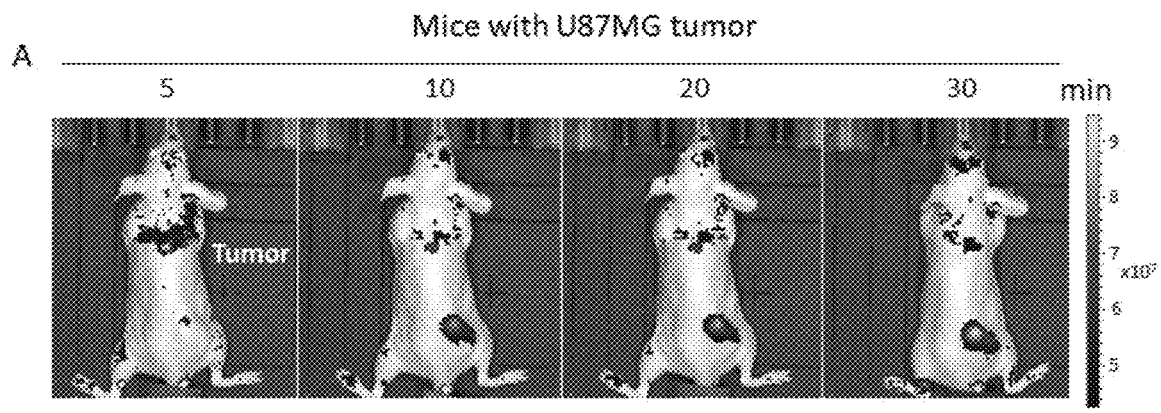
Figure 7B:
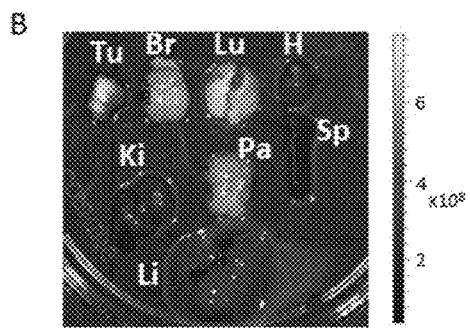

Fluorescence Imaging of hNQO1 in U87MG Tumor-Bearing Mice. With the prominent performance of NQ-DCP in cellular fluorescence imaging, the inventors further applied this probe to evaluate its capacity for the noninvasive fluorescence imaging of hNQO1 in vivo. NQ-DCP (10 mg/kg, 50 µL) was intravenously injected into sub-cutaneous U87MG tumor-bearing mice. The whole-body fluorescence was imaged with a Caliper IVIS Spectral imaging system. As shown in FIG. 7A, mice injected with NQ-DCP intravenously showed a gradual increase in fluorescence in the U87MG tumor, with the maximum fluorescence observed at 30 min. The host organs and tumor from the mice administered with NQ-DCP were harvested and their fluorescence was analyzed ex vivo using the IVIS to confirm the tumor-selective targeting ability of NQ-DCP. Fluorescence signals were selectively observed in the tumor and not in any other major organs such as the lung, heart, spleen, kidney, liver, brain, and pancreas (FIG. 7B). The application of NQ-DCP to image hNQO1 activity was also investigated in intracranial U87MG tumor-bearing mice. Tumor xenografts were established by implanting exponentially growing U87MG-Luc cells by stereotaxic injection into mice brain and the tumor growth was assessed by quantitative bioluminescence using IVIS (in vivo imaging system) (FIG. 7C). The inventors were not able to observe any fluorescence signal by systemic injections of the probe in intracranial tumors; this is perhaps due to the inability of the NQ-DCP to cross the blood-brain barrier. Therefore, the inventors performed intracranial injection of NQ-DCP (100 µM, 5 µL) to both healthy and tumor-bearing mice, the brain was isolated after 30 min and fluorescence images acquired. As shown in FIG. 7D, a bright fluorescence signal observed from the tumor-bearing mouse brain and no fluorescence from the control healthy mouse brain.

The present invention includes the development of hNQO1-activatable pro-fluorogenic probes that target the elevated hNQO1 found in solid tumors is useful for understanding enzymatic processes at the molecular level and developing tools to determine borders between diseased and healthy tissue during surgery. Consistently, based on the different levels of the hNQO1 present in cancer and normal cells, the catalytic property of NQO1 has been recently exploited for the development of effective fluorescent probes for cancer detection (Table 1) [23-31]. By exhibiting a small Stokes shift, the existing hNQO1 detecting fluorescent probes based on the rhodamine, fluorescein, cyanine, Nile red and BODIPY dyes reabsorb emitted photons, and lead to undesired background interferences. To overcome this problem, great efforts have been directed to develop fluorophore probes with a large Stokes shift ($\Delta\lambda \geq 80$ nm). Here, the inventors successfully developed a biocompatible, cell permeable and highly specific NQO1-responsive turn-on fluorescent probe (NQ-DCP; FIG. 1A) with a large Stokes shift to detect cancer cells. In the design of the present invention, Quinone propionic acid moiety was chosen as the enzyme active trigger and dicyanoisophorone group utilized as the chromophore due to its striking characteristics in terms of photophysical characteristics and biocompatibility.

The spectral character of NQ-DCP in response to hNQO1 was initially measured using both the UV-vis-absorption and fluorescence emission spectra upon the probe's incubation with hNQO1 in PBS buffer in the presence of 100 µM NADH. The fluorescent spectra (FIG. 2B) indicated that NQ-DCP was initially non-fluorescent and upon treated with hNQO1 had a significant increase in fluorescence intensity indicating the hNQO1 enzyme triggered cleavage reaction led to the release of highly fluorescent DCP (FIG. 1B). The release of DCP in the presence of hNQO1 was further confirmed with HPLC analysis (FIG. 1C). The fluorescence intensity of the probe was varied upon addition of different concentrations of hNQO1 (0-2.5 µg/mL) and the fluorescent signal intensities (FIG. 2C) were linearly proportional to hNQO1 concentration (FIG. 2D). Subsequently, the fluorescent intensity at 565 nm increased rapidly in a time-dependent manner and then obtained a maximum intensity in approximately 30 min (FIG. 3A,B). To rule out possible activation of NQ-DCP by various enzymes and biomolecules present in mammalian cells, the fluorescence response of NQ-DCP solutions were exposed to GSH, ALDH, GGT, GPx, APE1, CBS, CTSL, NTR, and NADH alone or in combination of hNQO1. As FIGS. 3C and D illustrated, only hNQO1 could induce a remarkable fluorescence enhancement, whereas, other species exhibited a negligible fluorescence. Incubation of NQ-DCP with hNQO1 in the presence of its specific inhibitor, ES936 completely blocked the NQ-DCP fluorescence (FIG. 3E).

Figure 4C:
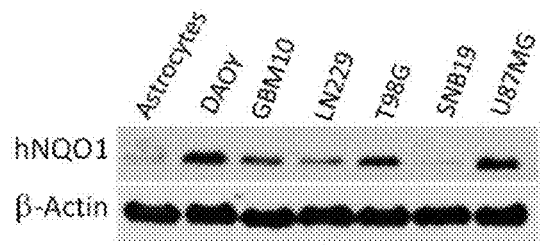
Figure 4B:
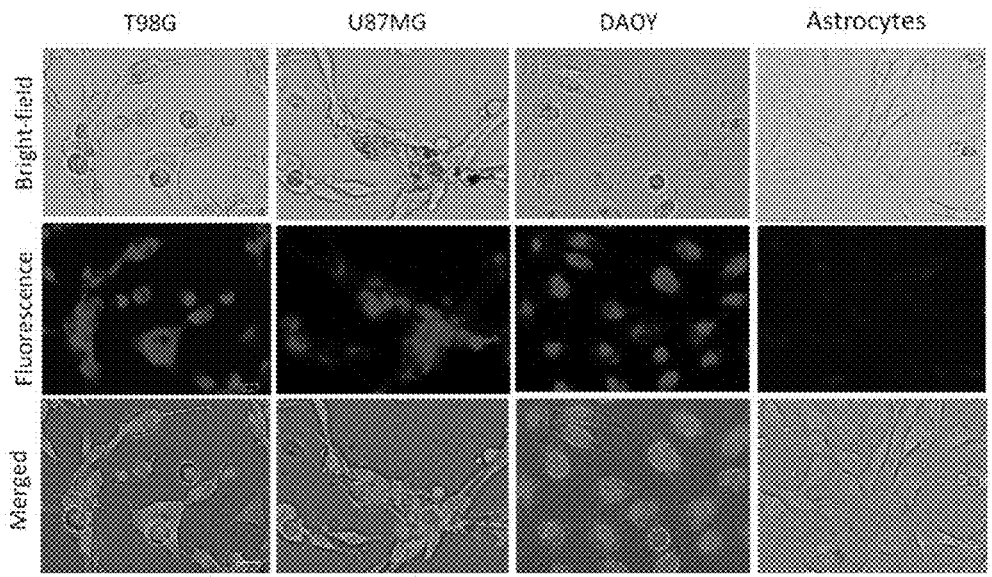
Figure 5A:
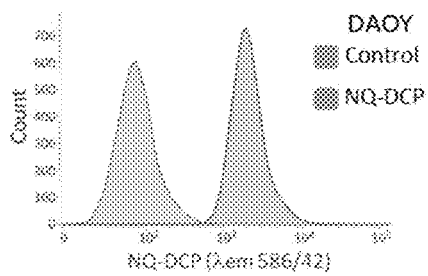
FIGS. 5A to 5D. Flow cytometry assays of NQ-DCP activation by NQO1-positive cell lines (5A) DAOY and (5C) T98G. (5B, 5D) Bar diagram represents the mean fluorescence intensities of three independent experiments. Assays were performed by counting 1×10$^4$ cells that had been exposed to 10 µM NQ-DCP probe for 1 h; $\lambda_{em}$=586/40 nm.
Figure 5B:
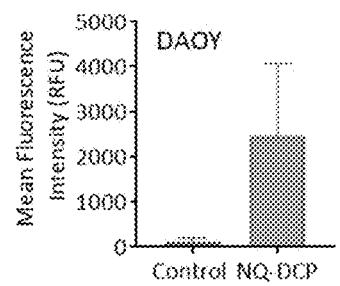
Figure 5C:
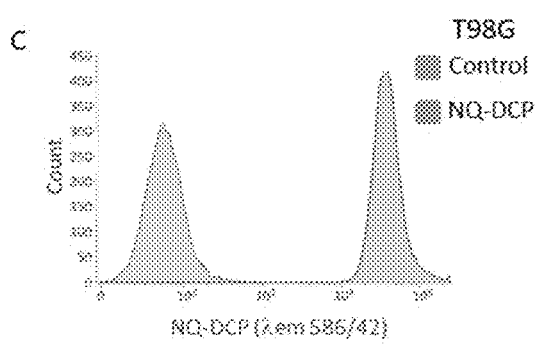
Figure 5D:
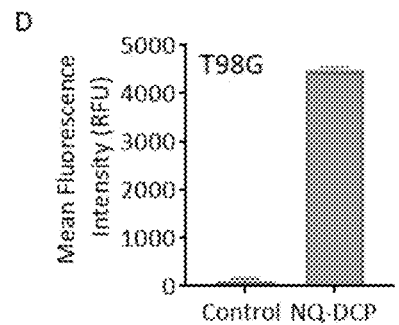

Considering the excellent sensing properties of the probe in an in vitro system, the inventors further studied the applicability of NQ-DCP to identify and differentiate tumor cells based on the presence of hNQO1 activity. Before cellular application, the cytotoxicity of the probe was evaluated in both normal and cancer cells and confirmed its biocompatibility (FIG. 4A). As shown in FIG. 4B, intense fluorescence was found in hNQO1 positive DAOY, T98G, and U87MG cells and no signals were observed from the hNQO1 negative normal cells. These observations indicated that the NQ-DCP is cell membrane permeable and the probe was readily activated by intracellular hNQO1 (FIG. 4C). Simultaneously, the flow cytometry analysis showed that NQ-DCP has the ability to differentiate tumor cells based on hNQO1 activity in fluidic streams (FIG. 5). The importance of hNQO1 for enzymatic activation the NQ-DCP probe was verified by pretreatment of cells with ES936, a selective inhibitor of hNQO1 and no fluorescence was found in hNQO1 inhibited cells after addition of NQ-DCP (FIG. 6A). To further demonstrate the difference in fluorescence signal observed in the cell images is indeed caused by hNQO1 activity level, the fluorescence turn-on of NQ-DCP was evaluated in an hNQO1 knockdown T98G cell line. As shown in FIG. 6B, limited or no fluorescence was observed after hNQO1 silencing.

Having demonstrated successful detection of upregulated hNQO1 activity within various cancer cell lines, the inventors further demonstrated the use of NQ-DCP probe for in vivo identification of tumors in an animal model. As shown in FIG. 7A, after the subcutaneous U87MG tumor-bearing mice were intravenously injected with NQ-DCP, a strong fluorescence response was observed in the tumor region of the mice in a time-dependent manner with a high tumor to background ratio. Ex vivo imaging of an alignment of individual mouse organs, demonstrated the presence of fluorescence signals only in the tumor bearing organs and not in other selected major organs indicated the preferential and selective accumulation and activation of NQ-DCP in the tumor tissue (FIG. 7B). These observations demonstrate that the probe of the present invention accumulates fluorescent probes in tumor cells mediated by tumor hypoxia and an enhanced permeability retention (EPR), both characteristics of the aberrant tumor vasculature [41]. To better mimic the clinical scenario, the present inventors also tested the probe in intracranial xenografts in nude mice by injecting U87MG cells (FIG. 7C), and the probe was injected into the brain. The ex vivo fluorescence imaging (FIG. 7D) showed that NQ-DCP was specifically activated by the tumor-bearing brain indicating the selective activation of the dye in the presence of hNQO1. These observations demonstrate that NQ-DCP is an effective fluorogenic probe for non-invasive and real-time imaging of hNQO1 activity in brain tumors during surgery.

Instruments and Materials. Fluorescence measurements were performed on a Hitachi F-2500 Fluorescence spectrophotometer (Hitachi-Science &Technology, Shizuoka, Japan) in a 10 mm standard cell with both excitation and emission slit widths of 10 nm. High-performance liquid chromatography (HPLC) was performed on Agilent HPLC instrument. IVIS Lumina XR Imaging system (Caliper Life Sciences, Inc., Waltham, MA, USA) was used for the in vivo imaging. The BD LSRFortessa™ cell analyzer (BD Biosciences, San Jose, CA, USA) was used for the flow cytometric analysis. 0.1% of BSA containing PBS with pH 7.4 was used for NQ-DCP spectroscopic measurements. The incubation of NQO1 with NQ-DCP in the presence of NADH was carried out on a shaker at 37° C. Bio-rad ZOE fluorescent cell imager (Bio-Rad Laboratories, Hercules, CA, USA) was used for the fluorescent microscopy. All chemicals and solvents used in syntheses were purchased from Sigma-Aldrich (St. Louis, MA, USA) or Fisher Scientific (Hampton, NH, USA) and used without further purification. NQO1 siRNA (h) (sc-37139) and NQO1 (A180) (sc-32793) antibodies were purchased from Santa Cruz (Santa Cruz Biotechnology Inc, Dallas, TX, USA). All cell lines were purchased from ATCC (American type cell culture collection). Immunodeficient NCG was purchased from Charles River Laboratories (Wilmington, MA, USA). Female athymic nude mice (nu/nu, 4-6 weeks) were purchased from Charles River Laboratories (Wilmington, MA, USA).

Spectroscopic Methods. For absorption and fluorescence measurements, all samples were first dissolved in 100% DMSO to obtain 10 mM stock solutions and then diluted to desired concentrations in PBS buffer containing 0.1% BSA for measurement. All spectroscopic measurements were performed under physiological conditions (pH 7.4 at room temperature. hNQO1 specific NQ-DCP activation was performed under philological conditions (PBS with 0.1% of BSA at 37° C.) in the presence of 100 µM NADH for 30 min. Time-dependent fluorescent intensity changes for different concentrations of NQ-DCI in the presence of NQO1 (2.0 µg/mL) and 100 µM NADH were measured using Hitachi F-2500 Fluorescence spectrophotometer ($\lambda_{ex}$=420 nm and $\lambda_{em}$=565 nm).

Selectivity Evaluation. To study the interference, NQ-DCP was incubated with various biologically relevant analytes such as thiols and other enzymes for 30 min with or without the addition of 100 µM NADH. Fluorescence spectra were analyzed to determine NQ-DCP specificity against hNQO1.

Evaluation of Inhibitor Efficiency. To evaluate the inhibitory efficiency of ES936 towards hNQO1 under in vitro conditions, different concentrations of ES936 (0-100 nM) incubated with 2.0 µg/mL of NQO1, 100 µM NADPH in PBS with 0.1% BSA (pH 7.4) at 37° C. Fluorescence emission was recorded after 30 min of incubation ($\lambda_{ex}$=420 nm).

Cell Culture, Fluorescence Imaging, and Flow Cytometry Analysis. Brain tumor cells and astrocytes were grown in Dulbecco's modified Eagle's (DMEM) medium containing 10% Fetal Bovine Serum and 1% penicillin/streptomycin in a humidified atmosphere of 5% $CO_2$ at 37° C. For fluorescence imaging, initially, cells were seeded into 6-well plate and cultured overnight in respective media at 37° C. Media was replaced with fresh medium containing 10 µM NQ-DCP and incubated at 37° C. for 60 min and then the medium was replaced with PBS and live cells were imaged using a fluorescence microscope. For inhibitor study, cells were pretreated with NQO1 inhibitor ES936 (100 nM) for 6 h before adding the NQ-DCP. For determining endogenous hNQO1 activity in cancer cells using flow cytometry, about $10 \times 10^4$ cells were incubated with 10 µM of NQ-DCP for 60 min and were analyzed using flow cytometry.

Knockdown of NQO1 by Small Interfering RNA (siRNA). NQO1 siRNA (a pool of 3 target-specific 19-25 nt siRNAs, Santa Cruz Biotechnology, Inc., (Dallas, TX, USA) and scrambled siRNAs were introduced into cells using the X-tremeGENE siRNA transfection reagent (Roche, Basel, Switzerland) according to the manufacturer's instructions with 80 pmol of NQO1 siRNA and 10 µl of transfection reagent per well of a six-well plate for T98G cells.

Immunoblotting. Cells were lysed in Cell Lysis Buffer (Cell Signaling, 9803) containing protease inhibitor and used for the immunoblotting. The protein concentration was estimated using the Bradford reagent (Bio-Rad, Hercules, CA, USA). Cell lysates with identical amounts of protein were fractionated by SDS-PAGE, and the proteins were electrophoretically-transferred to the polyvinylidene difluoride (PVDF) membranes. The hNQO1 and β-actin monoclonal antibodies and corresponding secondary antibodies were used for NQO1 protein detection.

In Vivo Bioimaging. The study was approved by the Institutional Animal Care and Use Committee (IACUC), Texas Tech University Health Sciences Center: Protocol No. 07050 entitled "Chemoprevention and Chemotherapy via MGMT"; Latest approval date: 28 Jul. 2018, valid through 28 Jul. 2019.

Four-week-old male and female NCG and athymic nude mice were housed in a micro ventilated caging system in a sterile environment and fed ad-libitum with standard irradiated research rodent diet and water. To detect endogenous NQO1 activity, NQ-DCP (10 mg/kg) was dissolved PEG-400:EtOH:saline (57.1:14.3:28.6, v/v/v) and 50 µL given through intravenous injection and animals were imaged using IVIS Lumina XR Imaging system. To establish U87MG xenografts, a total of $5 \times 10^6$ cells (in 0.1 mL) were subcutaneously injected into the right inguinal area of the athymic nude mice. For establishing the orthotopic brain tumor model, the animals were anesthetized using 2% isoflurane and positioned in a Benchmark (Leica) stereotactic instrument [42]. A 27-gauge needle was then used to drill a burr hole into the skull 0.5-mm anterior and 2-mm lateral to the bregma. U87MG-Luc2 cell suspension ($2 \times 10^5$ cells in 5 µl PBS) was injected in the striatum at a depth of 5 mm from the dural surface over 10 min. These mice were imaged for bioluminescence five days post tumor inoculation and were observed for stable tumor growth for the next two weeks. To detect endogenous NQO1 activity, orthotopic brain tumor models, NQ-DCP (50 μM) was dissolved saline and 5 μL given through intracranial injection to both healthy and tumor-bearing mice. After 30 min of administration, brains were isolated and imaged using IVIS Lumina XR Imaging system.

In summary, this example shows the successfully developed of an effective hNQO1 substrate-dicyanoisophorone (NQ-DCP) probe that was rapidly turned on in the presence of the cancer-specific biomarker, hNQO1, to yield a reporter whose spectral properties were sufficiently different from those of the probe so as to allow for ready differentiation of hNQO1 enzyme positive cancer cells from the negative normal cells. Combining its favorable light-up fluorescence feature, high selectivity, long wavelength emission, large Stokes shift, low cytotoxicity, and good membrane permeability, the inventors applied NQ-DCP to achieve the real-time visualization of hNQO1 in live cells and mice. The characteristic target-to-background signal ratio (TBR) provided by the probe/reporter system allowed a facile microscopic detection and quantification cellular hNQO1 by flow cytometry. In addition, this fluorescent probe allowed a non-invasive visualization of hNQO1 in subcutaneous and in an orthotopic brain tumor-bearing mouse models. The data suggest that NQ-DCP could be an effective and promising fluorescent probe with applications in cancer bioimaging.

Example 2—Characterization of a Highly Specific NQO1-Activated Near-Infrared Fluorescent Probe and its Application for In Vivo Tumor Imaging The Near-infrared Fluorescence (NIRF) molecular imaging of cancer is known to be superior in sensitivity, deeper penetration, and low phototoxicity compared to other imaging modalities. In view of an increased need for efficient and targeted imaging agents, the inventors synthesized the NAD (P)H quinone oxidoreductase 1 (NQO1)-activatable NIR fluorescent probe (NIR-ASM) of the present invention by conjugating a dicyanoisophorone (ASM) fluorophore with the NQO1 substrate quinone propionic acid (QPA). The probe remained non-fluorescent until activation by NQO1, whose expression is largely limited to malignant tissues. With a large Stokes shift (186 nm) and a prominent near-infrared emission (646 nm) in response to NQO1, NIR-ASM was capable of monitoring NQO1 activity in vitro and in vivo with high specificity and selectivity. This example shows the use of the NIR-ASM to differentiate cancer cells from normal cells based on NQO1 activity using fluorescence microscopy and flow cytometry. Chemical and genetic approaches involving the use of ES936, a specific inhibitor of NQO1 and siRNA and gene transfection procedures unambiguously demonstrated NQO1 to be the sole target activating the NIR-ASM in cell cultures. The NIR-ASM probe of the present invention was successfully used to detect and image the endogenous NQO1 in three live tumor-bearing mouse models (A549 lung cancer, Lewis lung carcinoma, and MDMAMB 231 xenografts) with a high signal-to-low noise ratiometric NIR fluorescence response. When the NQO1-proficient A549 tumors and NQO1-deficient MDA-MB-231 tumors were developed in the same animal, only the A549 malignancies activated the NIR-ASM probe with a strong signal. Because of its high sensitivity, rapid activation, tumor selectivity, and nontoxic properties, the NIR-ASM can be used as an agent in clinical applications including imaging, diagnosis, surgery, tracking of metastasis, and treatment.

Figure 8:
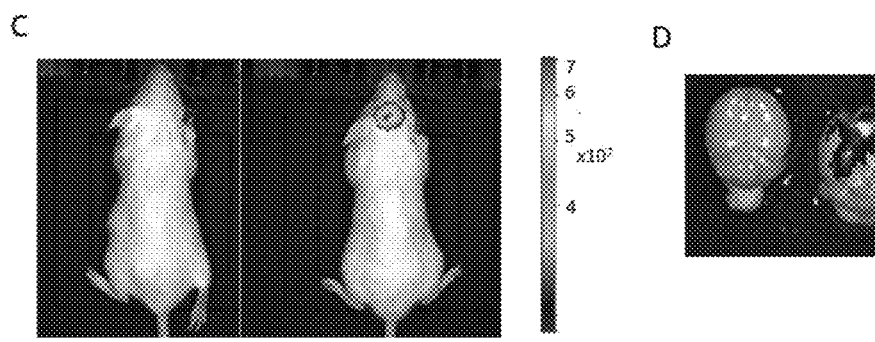
FIG. 8. Structure and application differences between NQ-DCP and NIR-ASM.
Figure 8:
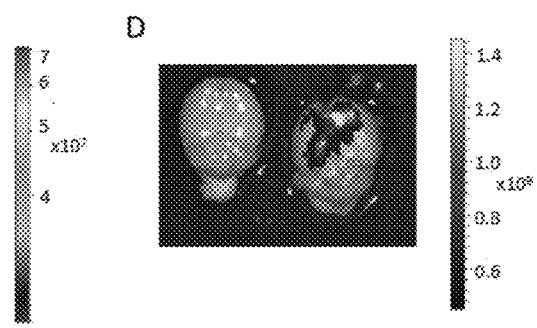
Figure 8:
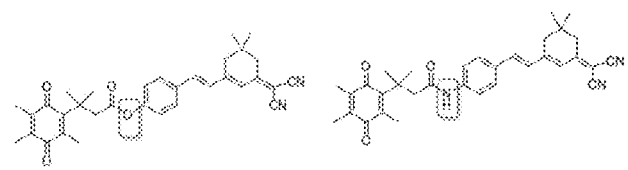

Near-infrared fluorescent (NIR) probes have distinct advantages over traditional fluorescent probes and become increasingly popular tools in the field of bioimaging.[38] The properties including low absorption of the NIR region by biological molecules leads to dramatically reduced levels of autofluorescence and deeper penetration into body tissues.[39] Despite the great implication of NQO1 as a biomarker for early diagnosis of cancer, none of the reported fluorescent probes have been evaluated for the non-invasive diagnosis of cancer in orthoptic cancer xenograft models. Taking these points into consideration and to overcome the limitations of NQ-DCP, the inventors developed a physiologically stable new NQO1 activatable 'turn-on' near-infrared fluorescent probe (NIR-ASM) for monitoring endogenous NQO1 activity and noninvasive cancer diagnosis (FIG. 8).

Figures 9A, 9B, 9C, 9D, 9E, 9F, 9G:
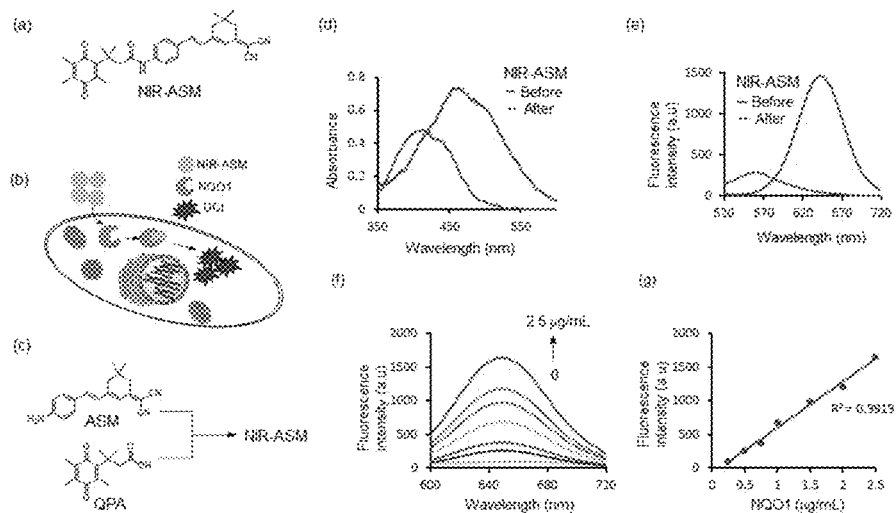
FIGS. 9A to 9G show. (9A) The structure of NQO1 activatable NIR fluorescent probe NIR-ASM. (9B) NIR-ASM activation and accumulation in NQO1 expressing cancer cells. (9C) Synthesis of NIR-ASM by coupling ASM with quinone propionic acid (QPA) in the presence of EDCI. (9D) absorbance and (9E) fluorescence emission spectra of NIR-ASM before (blue line) and after (red line) upon activated by NQO1 in the presence of 100 µM NADH in PBS with 0.1% BSA (pH 7.4). (9F) NQO1 concentration-dependent fluorescence ($\lambda_{max}$=646 nm) spectra of NIR-ASM in the presence of 100 µM NADH. (9G) The plot of fluorescence intensity versus NQO1 concentrations from 0.25 to 2.5 µg/mL. Experiments were performed in triplicate and averages were plotted.

Design, preparation, and characterization of the NIR-ASM fluorescent probe. Imaging agents emitting near-infrared fluorescence enable deeper penetration with low phototoxicity and high signal-to-background ratios due to minimal tissue auto-fluorescence, which is a prime requirement for in vivo imaging studies.[40,41] Accordingly, the inventors designed an NQO1 activatable near-infrared fluorescent probe (NIR-ASM) by attaching a trimethyl-lock QPA with (E)-2-(3-(4-aminostyryl)-5,5-dimethylcyclohex-2-en-1-ylidene)malononitrile (ASM) for molecular imaging of cancer cells in vivo (FIG. 9A). The fluorophore ASM was used in this study because of its strong NIR fluorescence signal with substantial Stokes shift (~190 nm), to eliminate background interferences by avoiding reabsorption of emitted photons. The inventors recognized that the initial fluorescence of NIR-ASM was significantly quenched due to the presence of QPA group capping at ASM via a stable amide bond, whereas NQO1 could cleave the amide bond and trigger the spontaneous elimination of dihydrocoumarin to liberate the ASM with remarkable NIR fluorescence enhancement. NQO1 is a ubiquitous cytosolic two-electron reductase that catalyzes the reduction of quinone substrates in the presence of NADH. The mechanism for visualizing NQO1 activity in living cells is shown in FIG. 9B. Upon interaction with NQO1 in the presence of NADH, QPA present in non-fluorescent NIR-ASM undergoes two-electron reduction to form an o-hydroxydihydrocinnamic acid derivative that undergoes rapid lactonization under physiological conditions to yield dihydrocoumarin, 6-hydroxy-4,4,5,7,8-pentamethylchroman-2-one (HPC) along with highly fluorescent ASM. NQO1 catalyzed the hydrolysis of NIR-ASM in solution was monitored using HPLC analysis and results showed that NIR-ASM (HPLC retention time, $T_R$=11.86 min) was nearly completely converted into ASM ($T_R$=10.81 min) after 30 min of incubation along with the generation of HPC ($T_R$=7.07 min). The synthesis of NIR-ASM was initiated from the preparation of fluorophore ASM and NQO1 substrate QPA according to the procedure outlined hereinbelow. ASM and QPA were coupled using EDCI as a catalyst and pyridine as a solvent (FIG. 9C). The chemical structures of these compounds were characterized by $^1$HNMR, $^{13}$CNMR and mass spectrometry. The purity of NIR-ASM was confirmed by HPLC.

Figures 10A, 10B, 10C, 10D, 10E:
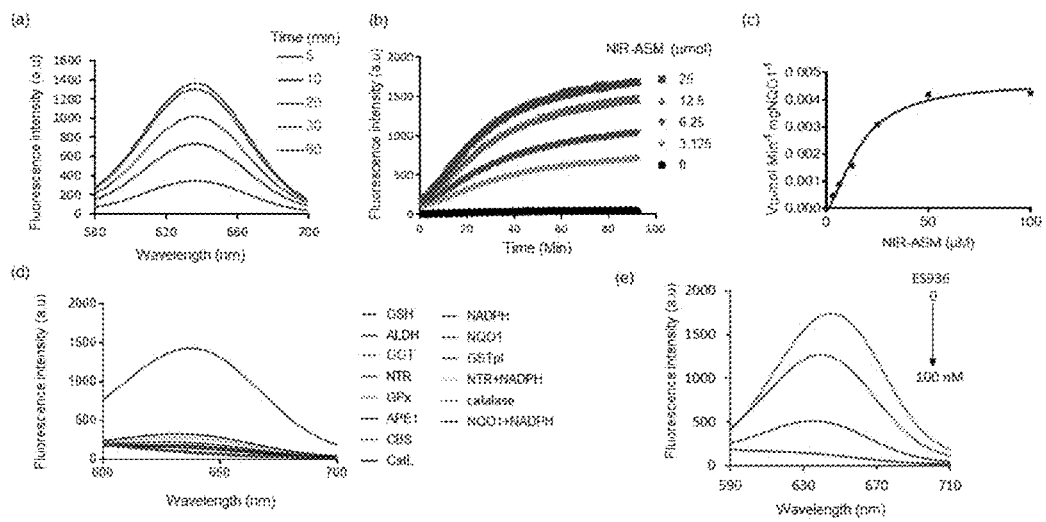
FIGS. 10A to 10E. (10A) Time-dependent NIR-ASM spectral changes initiated by the addition of NQO1 (2.5 µg/mL). (10B) Time-dependent fluorescent intensity changes for the probe NIR-ASM in the presence of different concentrations of NQO1 (0 to 25 µM). Experiments were performed in triplicate and averages were plotted. (10C) Kinetics plot of NQO1 (2 µg) towards NIR-ASM probe. Values shown are the average of 6 experiments. Assays were performed in 96 well plates at ex/em=460/646 nm in the presence of 100 µM NADH. (10D) Fluorescence response of NIR-ASM probe to various biologically relevant substrates. (10E) Effect of NQO1 inhibitor ES936 on NQO1 activation of NIR-ASM. All experiments were conducted with 10 mM NIR-ASM and 100 mM NADH in 0.1% BSA containing PBS (pH 7.4) at $\lambda_{ex/em}$=460/646 nm.

Fluorescent response of NIR-ASM towards NQO1. To unequivocally establish that NIR-ASM is a highly specific sensor for NQO1, the inventors first investigated its spectral properties were systematically studied in simulated physiological conditions 0.1% BSA containing PBS, BSA used as a stabilizing agent, pH 7.4) at 37° C., and the results are given in FIGS. 9D and 9E. As shown in FIG. 9D, NIR-ASM displays one absorption band at 403 nm. However, upon addition of NQO1, the absorption at 403 nm disappears and a prominent absorption at 465 nm emerges; Along with the bathochromic shift of UV/Vis absorption, a distinct color change from yellow to red was observed after 30 min of incubation with NQO1. Further, the NIR-ASM itself showed no fluorescence emission in the NIR region due to the presence of an amine in the form of the amide. However, the reaction of the probe with NQO1 produced a strong fluorescence emission band at 646 nm with a large Stokes shift (186 nm) (FIG. 9F), which is highly advantageous for bioimaging analysis, because of non-overlapping excitation and emission wavelengths. Next, the fluorescence response of NIR-ASM to NQO1 at varying concentrations (0-2.5 µg/mL) was studied. As shown in FIG. 9F, the fluorescence intensity increased gradually with increasing the NQO1 concentration and reached a plateau at 2.5 µg/mL of NQO1. Also, the fluorescence enhancement was directly proportional to the enzyme concentration in the range of 0.125-2.5 µg/mL ($R^2$=0.9919, FIG. 9G). The NQO1 detection limit (LOD) of NIR-ASM was calculated to be as low as 0.191 µg/mL, based on the standard deviation of the response (Sy) and the slope of the calibration curve (S) according to the formula: LOD=3.3(Sy/S). Furthermore, in the presence of NQO1, NIR-ASM exhibited a time-dependent fluorescence enhancement (FIG. 10A) with the emission peak at 646 nm reaching a maximum after 30 min. Similar time-dependent fluorescence increase was observed with the different concentrations of NIR-ASM to NQO1 (FIG. 10B).

Next, the kinetics of fluorescent product formation was assessed. The incubation of NIR-ASM (0-25 µmol) with NQO1 (2 µg/mL) and its cofactor NADH (100 µM) exhibited a steady increase in the fluorescence suggesting a relatively fast rate of production of ASM (FIG. 10C). From this experiment, the initial rate of ASM formation, V (µmol $min^{-1}$ µg $NQO1^{-1}$), was calculated and then plotted as a function of NIR-ASM concentration (FIG. 10C). Apparent kinetic parameters were obtained by fitting the data in FIG. 10C to Michaelis-Menten kinetics, namely, the Michaelis constant (Km)=33.82±0.45 µM, maximum velocity (Vmax)=0.00419±0.00003 µmol $min^{-1}$ mg $NQO1^{-1}$, catalytic constant (kcat)=13.01 $min^{-1}$, and catalytic efficiency (kcat/Km)=3.85×$10^5$ $M^{-1}$ $min^{-1}$. Taken together, the data suggest NIR-ASM could be applied as a "turn-on" fluorescent sensor with a sensitive response to NQO1.

Selectivity of NIR-ASM. The selectivity of NIR-ASM probe was studied by examining its reactivity towards various biomolecules and antioxidant enzymes such as the glutathione, aldehyde dehydrogenase 1, gamma-glutamyl transferase, glutathione peroxidase, apurinic/apyrimidinic endonuclease, cystathionine-β-synthase, cathepsin L, glutathione S-transferase, NADH alone and the combination of nitroreductase and NQO1. The probe NIR-ASM demonstrated high selectivity for NQO1 over the other enzymes/substrates tested, fluorescence resulted from the specific cleavage of QPA by NQO1 in the presence of its co-factor NADH (FIG. 10D). Next, the specificity for NQO1 was characterized by monitoring the fluorescence of NIR-ASM (10 mM) following incubation with NQO1, NQO1 pretreated with its inhibitor ES-926 (0-100 nM) a well-known NQO1 inhibitor.[42] As represented in FIG. 10E, ES936 effectively suppressed the fluorescence response in a concentration-dependent fashion, indicating the NQO1-dependent fluorescence response.

Figures 11A, 11B, 11C:
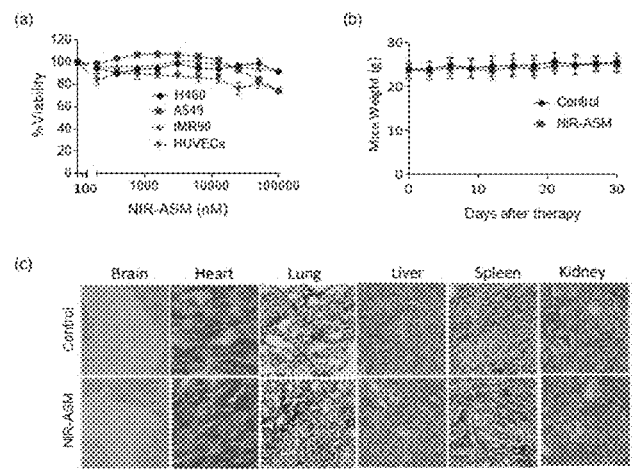
FIGS. 11A to 11C. (11A) cytotoxicity of NIR-ASM against both cancer (A549 and H460) and normal (HUVECs and IMR90) cells. Cytotoxicity was analyzed by resazurin reduction assay by treating with 10 different concentrations of the NIR-ASM. (11B) Animals were monitored for changes in body weight as a surrogate marker for toxicity after administration of 10 mg/Kg of NIR-ASM for 5 days a week for 4 weeks. (11C) Lack of host toxicity as indicated by the H&E staining of major organs of mice treated with NIR-ASM compared to vehicle-treated (control) mice.

Assessment of NIR-ASM biocompatibility. Inspired by the excellent photophysical properties of NIR-ASM in monitoring the NQO1 activity in vitro, the inventors determined the biocompatibility of NIR-ASM both in vitro and in vivo before using for endogenous applications. The cytotoxicity of NIR-ASM was initially evaluated in cultured non-small-cell lung cancer cell lines A549 and NCI-H460, normal cells including lung fibroblasts (IMR 90) and human umbilical vein endothelial cells (HUVECs) to evaluate its biocompatibility using resazurin reduction assay.[43] The results revealed that NIR-ASM was not toxic to both normal and cancer cells even at higher concentrations (up to 100 µM) (FIG. 11A). Further, to evaluate NIR-ASM tolerability and toxicity in vivo, CD1 mice were grouped for the administration of vehicle (PEG:$H_2$O:EtOH) alone or 5 mg/kg of NIR-ASM five times a week for five weeks. The average mouse weights were monitored as a surrogate marker to the toxicity. As shown in FIG. 11B, there were no remarkable changes in the average body weights, suggesting that the NIR-ASM treatment did not lead to overt toxicity of host tissues. Furthermore, there were no significant differences in the histological features among the NIR-ASM treatment and control groups in any of the tissues including the brain, heart, lung, liver, spleen, and kidney (FIG. 11C); these data indicate that NIR-ASM is unlikely to exert any adverse effects in the host at therapeutically relevant doses.

Figures 12A, 12B, 12C:
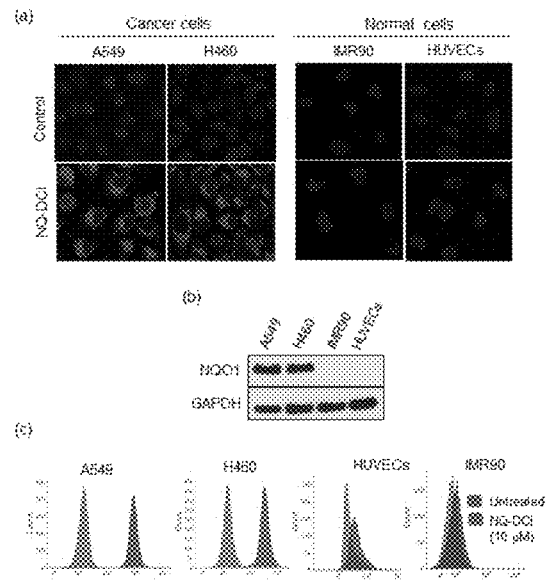
FIGS. 12A to 12C. (12A) Fluorescence images of NQO1-positive cancer cells NQO1-negative normal cells after incubation of 10 μM NIR-ASM for 1 h. The cell nuclei were counterstained by the Hoechst 33342 dye. (12B) Western blot showing the expression of NQO1 in cancer cells in comparison to the normal cells, GAPDH was used as a loading control. (12C) Flow cytometry assays were performed to determine NIR-ASM activation by NQO1-positive and negative cell lines. Assays were performed by incubating with 10 μM of NIR-ASM for 2 h and counting $1×10^4$ cells at $\lambda_{ex}$=488 nm, $\lambda_{em}$=617/40 nm.

Detection of NQO1 in live cells. Inspired by the excellent biocompatibility, the inventors investigated its performance in both NQO1 expressing cancer cells (A549, H460) and NQO1 non-expressing normal cells (IMR90, HUVEC). All cells were incubated with NIR-ASM (10 µM) for 60 min, washed with PBS and were imaged under a confocal microscope after counterstaining the nuclei with Hoechst 33342 (FIG. 12A). The A549 and H460 cells produced a bright NIR fluorescence signal, whereas the normal cells did not show any fluorescence. The higher expression of NQO1 protein in A549 and H460 cells and its absence in normal cells, IMR90 and HUVEC as found with western blot analysis correlated with the probe reactivity in cells (FIG. 12B). These results further confirm the cell permeability of the NIR-ASM and its reaction with the intracellular NQO1 enzyme. Cell sorting using flow cytometry is a well-established technology in clinical diagnostics and biomedical research. To assess the applicability of the NIR-ASM to rapidly detect and quantify in both cancer and normal cells based on NQO1 expression, the probe was incubated with cell suspensions for 60 min, and about 1×$10^4$ cells were analyzed on a flow cytometer. The resulting histograms for all the cell lines are shown in FIG. 12C. A high-intensity unimodal distribution of signals was obtained for NIR-ASM activation in each of the two NQO1-positive cancer cell lines (A549 and H460), while the negative normal cell lines IMR90 and HUVECs produced minimal fluorescence, thus confirming a rapid and detectable activation of the probe in A549 and H460 cells. Importantly, the sustained low fluorescence observed with the normal cells indicated the intracellular stability of NIR-ASM without any non-specific activation. These results clearly demonstrate that NIR-ASM has the ability to quantitatively detect endogenous NQO1 and can be used to rapidly differentiate tumor cells in fluidic streams.

Figures 13A, 13B, 13C, 13D, 13E, 13F, 13G:
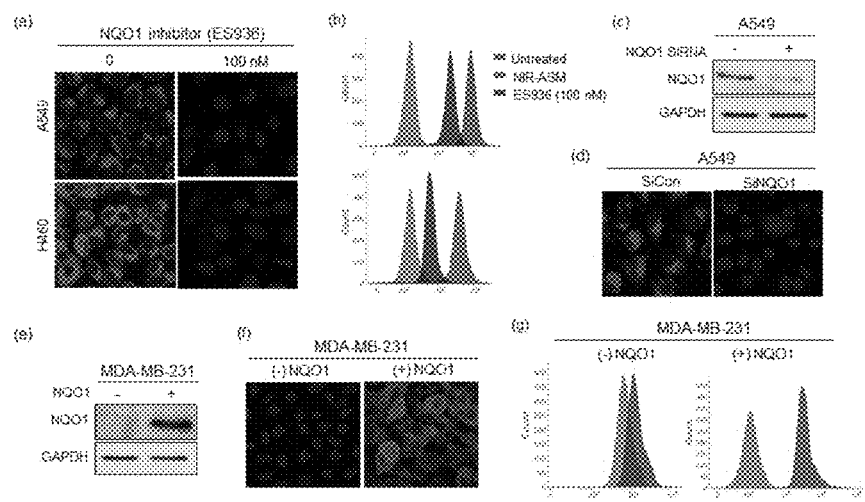
FIGS. 13A to 13G. (13A, 13B) Effect of NQO1 inhibitor ES936 (100 nM) on NIR-ASM fluorescence. Fluorescent microscopy (13A) and flow cytometry (13B) analysis of cells after treating with NIR-ASM (10 μM) for 1 h in the presence and absence of ES936 (100 nM). (13C, 13D) Western blot showing the siRNA knockdown of NQO1 and its effect on the activation of NIR-ASM in A549 cells. (13E) Western blot showing the transfection NQO1 into the NQO1 null MDA-MB-231 cells. (13F, 13G) fluorescent microscopic images and flow cytometric analysis of wild-type (NQO1 negative) and NQO1 gene transfected (NQO1 positive) cells after incubating 10 μM NIR-ASM for 1 h.

Chemical and genetic approaches confirm the specificity of NIR-ASM for NQO1 in live tumor cells. A fluorescence probe with high sensitivity, simple operation, and excellent specificity will be an asset for the detection of NQO1 in situ. To assess the substrate selectivity of NIR-ASM for NQO1, both A549 and H460 cells were pretreated with 100 nM of NQO1 inhibitor ES936 for 6 h, before incubating with 10 µM NIR-ASM. ES936 completely blocked the NIR-ASM fluorescence when compared to the untreated cells (FIG. 13A). The effect of ES936 on endogenous NQO1 activity and subsequent reactivity with NIR-ASM was also determined by flow cytometry. The histograms in FIG. 13B, again show that the NIR-ASM induced fluorescence intensity was significantly decreased in ES936 pretreated tumor cells. In addition, as shown in FIG. 13C, a specific siRNA that silenced NQO1 gene expression more than 70% induced almost a total loss of NIR-ASM fluorescence compared with the control after 60 min incubation (FIG. 13D), suggesting that NQO1 was indeed responsible for the activation NIR-ASM fluorescent probe. To further demonstrate the difference in fluorescence signal observed in the cell images is certainly caused by NQO1 activity levels, the inventors transfected the NQO1-negative MDAMB-231 breast cancer cells with an expression vector encoding a full-length human NQO1 protein followed by evaluation of NIR-ASM in parent and transfected cells. The presence of NQO1 protein in the transfected MDA-MB-231 cells and its absence in the untransfected control was confirmed by immunoblotting (FIG. 13E). Subsequently, the NQO1-negative and positive MDA-MB-231 cell lines were incubated with NIR-ASM and analyzed by fluorescence microscopy and flow cytometry for activation of the probe. No fluorescence was observed in control MDA-MB-231 cells, while intense fluorescence was evident after gene transfection (FIGS. 13F and 13G). These data unambiguously confirm that the NIR-ASM probe is activated to the fluorescent ASM reporter depending on the levels of NQO1 protein present in tumor cells, thereby allowing accurate identification of NQO1-positive cells.

Figures 14A, 14B, 14C, 14D:
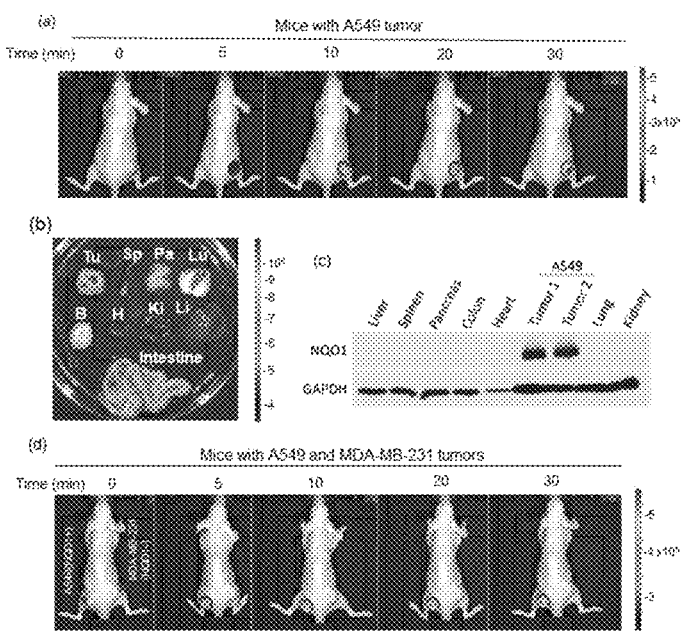
FIGS. 14A to 14D. (14A) Fluorescence imaging of endogenous NQO1 activity in A549 tumor-bearing nude mice after NIR-ASM (5 mg/kg, 50 μL) intravenous administration. (14B) After 30 min of NIR-ASM administration, ex vivo fluorescent imaging of dissected organs such as the spleen (Sp), Pancreas (Pa), Lungs (Lu), Brain (Br), Heart (H), Kidneys (Ki), Liver (Li) and intestine along with tumor (Tu). (14C) Immunoblot analysis showing the presence of NQO1 only in tumor lysates compared to other organs. (14D) In vivo fluorescence imaging of nude mice bearing both NQO1 positive (A549) and NQO1 negative (MDA-MB-321) tumors after intravenous administration of NIR-ASM. In vivo imaging performed with IVIS Lumina XR Imaging system using excitation/emission filters of 500/640 nm. The scale indicates fluorescence intensity in terms of radiant efficiency.

In vivo real-time imaging of NQO1 in xenografts using NIR-ASM. In vivo real-time imaging offers a powerful tool for accurately diagnosing disease and suspicious lesions with valuable spatiotemporal precision. Having demonstrated the excellent specificity and performance of NIR-ASM in cultured cells, the inventors determined its use in real-time imaging of NQO1 activity in tumor-bearing mice. Tumor xenografts were established by implanting exponentially growing lung cancer cells (A549) subcutaneously into nude mice. When tumor growth reached the log phase, NIR-ASM (5 mg/kg in PEG:$H_2O$:EtOH (6:3:1)) was given intravenously and subjected to whole-body fluorescence imaging using an In Vivo Imager (IVIS). As shown in FIG. 14A, a time-dependent and gradual increase in fluorescence signal in response to NQO1 was observed in the A549 tumor region and reached the plateau at 30 min. No signal was apparent in other organs of the animal. To confirm the tumor-selective targeting ability of NIR-ASM, the host organs and tumor from the mice administered with NIR-ASM were harvested and their fluorescence was analyzed ex vivo using the same IVIS. Fluorescent signals were observed only in the tumor and not in any other major organs including the lung, heart, spleen, kidney, liver, brain, pancreas and intestine (FIG. 14B). Furthermore, the lysates from the tumor and various organs were electrophoresed and western blotted using the NQO1 antibody. NQO1 protein at detectable levels was seen only in the tumor lysate and not in other tissues, thus, reinforcing the specificity of in-vivo imaging (FIG. 14C).

Additionally, to validate the NQO1-specific activation of NIR-ASM to generate fluorescence, the inventors generated NQO1-positive (A549) and -negative (MDA-MB-231) xenografts in the same animal by injecting the corresponding tumor cells on the left and right flanks of the nude mice respectively. When tumors reached a volume of 200 $mm^3$, NIR-ASM was administered through intravenous injection and the animals were imaged using the In Vivo imager. A gradual and productive fluorescence signal was observed only from the A549 tumor and no signal was discernible in the NQO1 negative MDAMB-231 tumors, again demonstrating the ability of our probe to distinguish between NQO1-positive and negative malignancies in real-time (FIG. 14D).

Figures 15A, 15B, 15C, 15D:
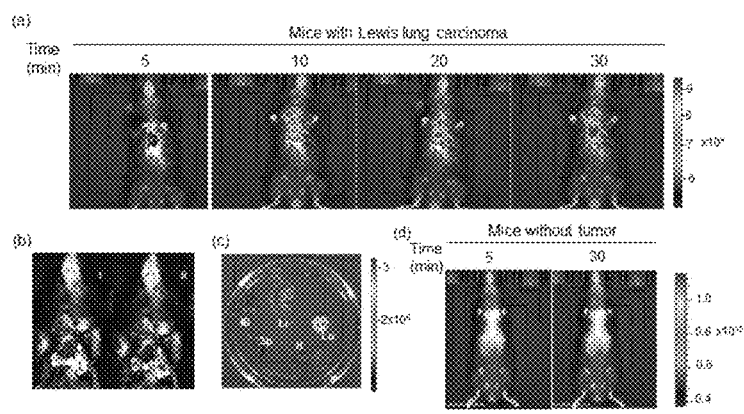
FIGS. 15A to 15D. In vivo real-time fluorescence imaging in Lewis Lung Carcinoma (LLC) bearing BALB/c57 mice after intravenous administration of NIR-ASM (5 mg/kg, 50 (15a) time-dependent increase in the fluorescence intensity reaching a maximum at 30 min. (15B) NIR-ASM illuminated lungs bearing LLC tumors with the minimal background; representative photograph (i) with markings of the heart (H), liver (Li) and Lungs (Lu) and composite image (ii) with fluorescence. (15C) Fluorescent imaging of ex vivo-dissected organs such as the spleen (Sp), Lungs (Lu), Heart (H), Kidneys (Ki), Liver (Li) after administration NIR-ASM at 30 min. (15D) In vivo fluorescence imaging of non-tumor-bearing mouse after intravenous administration of NIR-ASM. In vivo imaging performed with IVIS Lumina XR Imaging system using excitation/emission filters of 500/640 nm. The scale indicates fluorescence intensity in terms of radiant efficiency.

Whether still in-situ or already disseminated, early diagnosis of cancer is an essential requirement for successful therapy. Although NQO1 is expressed at higher levels in cancers compared to a diminished or absent status in normal tissues, the diagnostic potential of existing NQO1 specific fluorescent probes has not been realized. Therefore, the inventors evaluated the non-invasive diagnostic ability of NIR-ASM in a metastatic syngeneic lung cancer model to mimic the clinical situation. Lung cancer was established in C57BL/6 mice by injecting Lewis Lung carcinoma (LLC) cells ($0.5 \times 10^6$ per animal) intravenously. This cell line is highly tumorigenic and is primarily used to model metastasis as well as evaluate the efficacy of chemotherapeutic agents in vivo.[44] The LLC cells have ~80 units of NQO1 activity compared to <10 units in healthy mouse lungs.[45] Two weeks after the implantation, the animals received NIR-ASM (5 mg/kg) intravenously. As demonstrated by both in vivo and ex vivo NIRF imaging (FIGS. 15A and 15B), an intense fluorescent signal was observed from the tumor-bearing lungs, which was more than 100-fold higher NIRF signal intensity compared to other selected organs (FIG. 15C). Moreover, no fluorescence observed in the lungs of healthy mice after NIR-ASM administration (FIG. 15D). There are several routes for drug elimination from the body and the majority of drugs are eliminated by pathways that involve the kidneys. The fluorescence observed kidneys during ex vivo NIRF imaging indicating renal excretion might play an important role in eliminating NIR-ASM (FIG. 15C). In line with these data, the inventors found that NIR-ASM fluorescent probe can be ideal for non-invasive diagnosis and early detection of NQO1 positive tumors in vivo.

In summary, the inventors have developed an enzyme-activatable, cell-permeable, non-toxic and biocompatible 'turn-on' NIR fluorescent probe (NIR-ASM) that provides accurate detection and visualization of endogenous NQO1 activity both in vitro and an in vivo preclinical model of lung and breast cancers. The inventors also demonstrated that NIR-ASM was highly stable and could be specifically activated by NQO1 to generate NIR fluorescence with a large Stokes shift (186 nm). The NIR-ASM probe of the present invention displayed a highly selective response toward NQO1 and did not generate fluorescence in other NADH requiring antioxidant reactions. The probe successfully differentiated NQO1 expressing cancer cells from normal cells and was validated using an NQO1 inhibitor, specific siRNA for NQO1 and by forced expression of the NQO1 protein both in vitro and in vivo. The NIR fluorescence of the probe showed a fast response and allowed a noninvasive in vivo real-time visualization of NQO1 in two subcutaneous and an orthotopic lung cancer-bearing mouse models without auto-fluorescence. The results show that NIR-ASM is an effective NIR fluorescent probe for the detection, diagnosis, and treatment of cancers.

Materials and methods. All chemicals and solvents used in syntheses were purchased from Sigma-Aldrich or Fisher Scientific and used without further purification. NQO1 was purchased from Sigma-Aldrich (D1515). NQO1 siRNA (h) (sc-37139) and NQO1 (A180) (sc-32793) antibodies were purchased from Santa Cruz. All cell lines were obtained from ATCC (American type cell culture collection) The $^1$H, $^{13}$C NMR spectra were recorded on a Bruker-Avance 400 MHz Spectrometer. Chemical shifts (δ) are reported in ppm. ESI mass spectra were recorded on AB sciex QTRAP 5500 mass spectrometer. High-performance liquid chromatography (HPLC) was performed on an Agilent HPLC instrument. Peaks in NMR spectra are listed as singlet (s), doublet (d), triplet (t), or multiplet (m), and coupling constants (J) are reported in hertz (Hz). Fluorescence spectra were recorded on a Hitachi F-2500 Fluorescence spectrophotometer in a 10 mm standard cell with both excitation and emission slit widths of 10 nm. The incubation of NQO1 with NIR-ASM in the presence of NADH was carried out on a shaker at 37° C. IVIS Lumina XR Imaging system (Caliper Life Sciences, Inc.) was used for the in vivo imaging. The BD LSRFortessa™ cell analyzer was used for the flow cytometric analysis. A Nikon multiphoton microscope equipped with NIS-Elements C acquisition and analysis software was used for the fluorescence microscopy.

Spectroscopic measurements. NIR-ASM was dissolved with DMSO to prepare a stock solution, which was then diluted with enzyme reaction buffer (PBS containing 2.5 µg/mL, 100 µM NADH and 0.1% BSA) to prepare different concentrations of the probe for UV/Vis and fluorescence measurement. Time-dependent fluorescence intensity changes for different concentrations of NIR-ASM in the presence of NQO1 (2.5 µg/mL) and 100 µM NADH were measured using Clear bottom 96 well black plate and microplate reader. Fluorescence (ex. 460 nm and em. 646 nm) was quantitated every minute for 90 min with 20 seconds of shaking in between intervals.

Kinetic studies. Kinetic studies were performed using a microplate reader under philological conditions (PBS with 0.1% of BSA at 37° C.). The assay buffer contained 2 µg/mL of NQO1, 100 µM NADH and different concentrations of NIR-ASM (0-100 µM) in a total volume of 100 µL. Time-dependent fluorescence measurements were carried out to monitor the release of ASM by NQO1 activation of NIR-ASM ($\lambda_{ex/em}$ 460/646), and the data were collected every minute for 90 minutes. This assay was repeated two times in triplicate and the fluorescence readings were optimized to a standard curve of ASM of known concentration and calculated the velocity in terms of $\mu mol^{-1} \, min^{-1} \, \mu g$ NQO1. A plot of the velocities and NIR-ASM concentration was used to obtaining the apparent kinetic parameters Km and Vmax from nonlinear regression analysis and Michaelis-Menton constant using the GraphPad Prism.

NQO1 inhibitor efficiency evaluation. NQO1 inhibitor efficiency was evaluated using specific NQO1 inhibitor ES936 under in vitro conditions. 2.5 µg/mL of NQO1 was incubated with different concentrations of ES936 (0-100 nM) in the presence of 100 µM NADH at 37° C. Fluorescence emission was recorded after 30 min of incubation ($\lambda_{ex}$. 460 nm).

Cell culture. Non-small-cell lung cancer cell lines (A549 and H460) breast cancer cell line (MDA-MB-231) and human lung fibroblasts (IMR 90) were grown in Dulbecco's modified Eagle's (DMEM) medium supplemented with 10% Fetal Bovine Serum and 1% penicillin/streptomycin at 37° C. in a 5% $CO_2$/95% air incubator. Primary human umbilical vein endothelial cells (HUVECs) were grown in M199 medium, supplemented with 15% fetal bovine serum, 150 mg/ml endothelial cell growth supplement, 5 U/ml heparin sodium and 1× antibiotic/antimycotic solution (Gibco).

Knockdown of NQO1 by small interfering RNA (siRNA). NQO1 and scrambled or control siRNAs were introduced into cells using the X-tremeGENE siRNA transfection reagent (Roche) according to the manufacturer's instructions. 10 µl of transfection reagent was mixed with 80 pmol of siRNA and added to A549 cells in six-well plates. siRNA transfection efficiency was confirmed with Western blotting.

NQO1 plasmid transfection. Cells were seeded at 60% confluence in six-well plates 16 h before transfection with the desired plasmids. Transfections were carried using a plasmid expressing wild-type NQO1 (pCDNA3 NQO1-Flag, addgene, 61729) and X-tremeGENE DNA transfection reagent (Roche) according to manufacturer instructions. One µg DNA was used in each transfection and cell extracts were prepared 24 h post-transfection to confirm NQO1 protein expression by Western blotting.

Determination of NIR-ASM specificity towards NQO1. The specificity towards NQO1 was investigated by incubating NIR-ASM (10 µm) with various biologically relevant analytes such as glutathione (GSH, 1 mM), aldehyde dehydrogenase 1 (ALDH1A1, 2.5 µg/mL), gamma-glutamyl transferase (GGT, 10 U), glutathione peroxidase (GPx, 10 U), apurinic/apyrimidinic endonuclease (APE1, 10 U), cystathionine-β-synthase (CBS, 2 µg/mL), cathepsin L (CTSL, 2 µg/mL), glutathione S-transferase (GST-pi, 2 µg/mL), NADH (100 µM) alone and the combination of nitroreductase (NTR, 2 µg/mL) and NQO1 (2 µg/mL) for 30 min. Fluorescence spectra were analyzed to determine NIR-ASM specificity against NQO1.

Cell viability assays. NIR-ASM was evaluated for in vitro cytotoxicity in human cancer (A549 and H460) and normal (IMR90 and HUVECs) cell lines following a protocol of 72 h continuous drug exposure using resazurin reduction assay. The cell lines were grown in 96-well microtiter plates at a density of 5000 cells per well. The plates were incubated for 24 h prior to addition of NIR-ASM. Ten concentrations of NIR-ASM were evaluated in quadruplicate sets. Plates were incubated for a further 72 h and replaced with 20 µL resazurin 0.01% (w/v) containing the medium. After 2 h, the fluorescence was measured using a Tecan Reader (Infinite m200 Pro) at a 544 nm excitation and 590 nm emission.

Fluorescence imaging. Both cancer and normal cells were seeded into 6-well plates and cultured overnight in respective media at 37° C. Cells were treated with 10 µM NIR-ASM and incubated at 37° C. for 60 min. They were then treated with nuclear stain Hoechst 33342 for 5 min. Finally, the medium was replaced with PBS and the live cells were imaged using a multiphoton confocal fluorescence microscope ($\lambda_{ex/em}$=488/644 nm). For inhibitor study, cells were pretreated with NQO1 inhibitor ES936 (100 nM) for 6 h before adding the NIR-ASM.

Flow cytometry analysis. The endogenous NQO1 activity of cancer cells and normal cells was determined by flow cytometry after NIR-ASM exposure. Cells were incubated with 10 µM of NIR-ASM for 60 min, harvested by trypsinization and washed with PBS. For inhibitor study, cells were pretreated with NQO1 inhibitor ES936 (100 nM) for 6 h before adding the NIR-ASM. About $1 \times 10^4$ cells were analyzed by flow cytometry ($\lambda_{ex}$=488 nm).

Immunoblotting. Cells or tissues (100 mg/mL) were lysed in Cell Lysis Buffer (Cell Signaling, 9803) containing protease inhibitors and used for the immunoblotting. After estimating protein concentration using Bradford reagent (Bio-Rad, Hercules, CA), identical amounts of protein were fractionated by SDS-PAGE, and the proteins were electrophoretically-transferred to the polyvinylidene difluoride (PVDF) membranes. The hNQO1 monoclonal antibody was used for protein detection.

Hematoxylin and eosin (H&E) staining. The hematoxylin and eosin staining were performed as described previously. Briefly, freshly dissected tissues were snap freeze and store at −20° C. for overnight. Frozen tissues were cut into 9 mm slices, the sections were stained in Mayer's Hematoxylin and Eosin solution. Finally, the sections were dehydrated and mounted with Permount in a fume hood. The results were analyzed under a phase-contrast Olympus microscope (Olympus America Inc).

In vivo bioimaging. The animal study protocol was approved by the Institutional Animal Use and Care Committee (IACUC), Texas Tech University Health Sciences Center, Protocol number: 07050. All experimental protocols used in this study were approved by IACUC, Texas Tech University Health Sciences Center and all the methods were carried out according to the committee guidelines. Female athymic nude mice (nu/nu, 4-6 weeks) were purchased from Charles River Laboratories (Wilmington, MA, USA). BALB/c57 mice were provided by Dr. Constantinos Mikelis of our University. To establish A549 or MDA-MB-231 xenografts, a total of $5\times10^6$ cells (in 0.1 ml of serum-free media and Matrigel (1:1)) were subcutaneously injected into the flanks of the mice. For developing orthotopic lung cancer models, LLC cells ($0.5\times10^6$) were intravenously injected into the tail veins of female BALB/c57 mice. All animals were monitored for activity, physical condition, body weight, and tumor growth. To detect endogenous NQO1 activity, NIR-ASM was dissolved in a vehicle of composition, PEG-300:EtOH:saline (60:30:10, v/v/v) and given intravenously through tail vein injection. The animals were imaged at different time intervals with excitation/emission filters of 500/640 nm using the IVIS Lumina XR Imaging system. At the end of the experiments, the xenografted tumors, hearts, lungs, livers, kidneys, spleens, and brains were removed and imaged to confirm the signal locations. Fluorescence represented in log values of radiance is photons per second per square centimeter per steradian.

Synthesis of the highly specific NQO1-activated near-infrared fluorescent probe and its application for in vivo tumor imaging Materials and Methods. All chemicals and solvents used in syntheses were purchased from Sigma-Aldrich or Fisher Scientific and used without further purification. Galss TLC silica gel 60 F254 were purchased from EMD Millipore and used to perform thin layer chromatography. SilicaFlash P60 (230-400 mesh) purchased from Silicycle was used for the purification of products.

The $^1$H, $^{13}$C NMR spectra were recorded on a Bruker-Avance 400 MHz Spectrometer. Chemical shifts (δ) are reported in ppm. ESI mass spectra was recorded on AB sciex QTRAP 5500 mass spectrometer. High-performance liquid chromatography (HPLC) was performed on an Agilent HPLC instrument. Peaks in NMR spectra are listed as singlet (s), doublet (d), triplet (t), or multiplet (m), and coupling constants (J) are reported in hertz (Hz).

Synthesis of NIR-ASM. NIR-ASM was prepared as described in scheme 1.

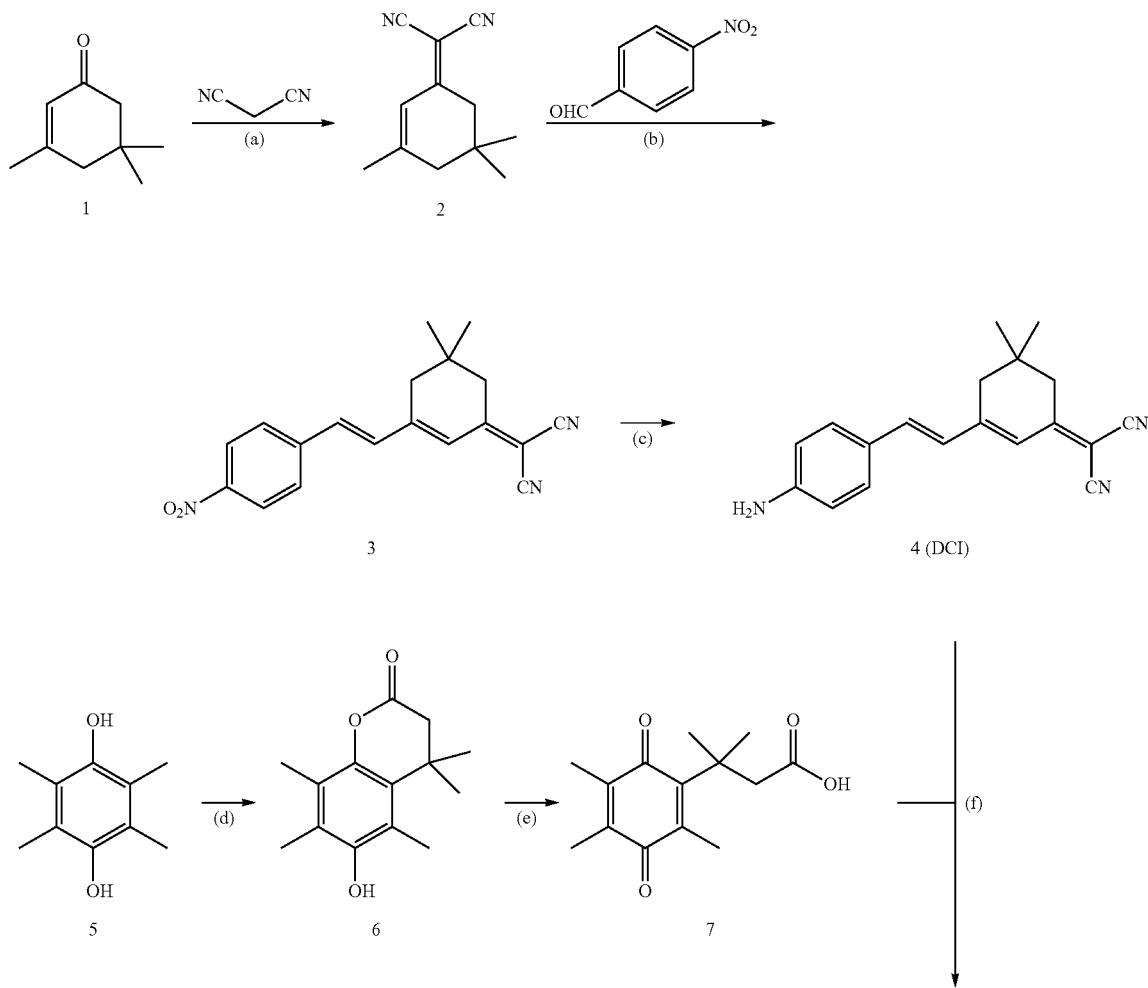

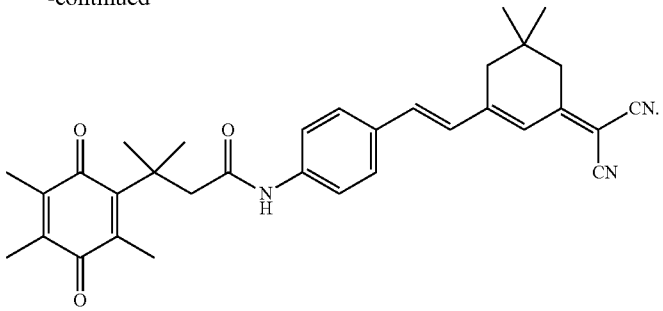

NQ-DCI

Reagents & conditions: (a) Ammonium acetate, acetic anhydride, acetic acid, toluene, reflux, 12 h; (b) piperidine, acetonitrile, 50° C., 6 h; (c) SnCl$_2$, HCl, ethyl acetate, 8 h; (d) methyl 3,3-dimethylacrylate, methanesulfonic acid, 70° C., 2 h; (e) NBS, acetonitrile, water, rt, 1 h; (f) EDC, pyridine, rt, 10 h.

Synthesis of Quinone propionic acid (QPA) (7): QPA was prepared from commercially available stating materials 2,3, 5,6-tetramethylbenzene-1,4-diol (5) and methyl 3,3-dimethylacrylate using methane sulfonic acid as a catalyst as presented in scheme 1.

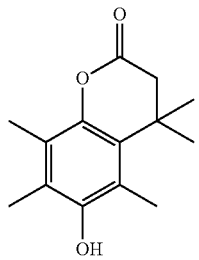

Synthesis of 6-hydroxy-4,4,5,7,8-pentamethylchroman-2-one (6): To a stirred solution of 2.25 g (13.5 mmol) of 2,3,5,6-tetramethylbenzene-1,4-diol (5) in 15 mL of methanesulfonic acid was added 1.98 mL (1.85 g, 16.2 mmol) of methyl 3,3-dimethylacrylate at room temperature. The reaction mixture was stirred at 70° C. for 2 h. After cooling to room temperature, the reaction mixture was diluted with 150 mL of water and extracted three 70 mL portions of dichloromethane. The combined organic extracts were washed with 100 mL of saturated NaHCO$_3$ solution, 100 mL of NaCl solution, dried over anhydrous Na$_2$SO$_4$ and concentrated under diminished pressure. The crude product was recrystallization from 30% CHCl$_3$ in hexanes gave compound 6 as white solid: yield 2.56 g (81%); $^1$H NMR (400 MHz, CDCl$_3$) δ 1.45 (s, 6H), 2.19 (s, 3H), 2.22 (s, 3H), 2.36 (s, 3H), 2.55 (s, 2H) and 4.75 (s, 1H); $^{13}$C NMR (100 MHz, CDCl$_3$) δ 12.3, 12.6, 14.5, 27.7, 35.5, 46.1, 118.9, 121.8, 123.4, 128.2, 143.5, 148.8 and 168.9. ESI MS (m/z): 234 (M$^+$)

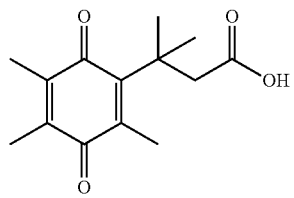 [SMILES: CC1=C(C)C(=O)C(C(C)(C)CC(=O)O)=C(C)C1=O]

Synthesis of 3-methyl-3-(2,4,5-trimethyl-3,6-dioxocyclohexa-1,4-dien-1-yl)butanoic acid (7, QPA) (7): To a stirred solution of 2.00 g (8.54 mmol) of compound 6 in a solution of 70 mL of acetonitrile and 30 mL of water was added 1.67 g (9.39 mmol) of N-bromosuccinimide at room temperature. After 60 min, acetonitrile was removed from the reaction mixture, the residue was extracted three 30-mL portions of dichloromethane. The combined organic layer was dried over anhydrous Na$_2$SO$_4$ and concentrated under diminished pressure. The crude product was purified by chromatography on a silica gel column. Elution with 4:1 hexanes-ethyl acetate afforded compound 7 as yellow solid: yield 1.64 g (77%); silica gel TLC R$_f$ 0.23 (7:3 hexanes/ethyl acetate); $^1$H NMR (400 MHz, CDCl$_3$) δ 1.43 (s, 6H), 1.92 (s, 3H), 1.95 (s, 3H), 2.13 (s, 3H) and 3.01 (s, 2H); $^{13}$C NMR (100 MHz, CDCl$_3$) δ 12.2, 12.6, 14.4, 29.0, 38.1, 47.4, 138.5, 139.2, 143.1, 152.1, 178.6, 187.6 and 191.0. ESI MS (m/z): 249.1 (M-1).

Synthesis of ASM 2-(3,5,5-trimethylcyclohex-2-en-1-ylidene) malononitrile (2): To a stirred solution of 2.25 mL (15.0 mmol) isophorone (1) and 1.49 g (22.5 mmol) of malononitrile in 50 mL toluene were added 0.29 g (3.75 mmol) of ammonium acetate, 0.5 mL of glacial acetic acid, and 1.0 mL of acetic anhydride. The reaction mixture was heated at 120° C. for 12 h under air atmosphere in the dark. Reaction mixture was allowing to cool to room temperature, solvent was removed under diminished pressure, neutralized with saturated sodium carbonate solution and extracted with three 30 mL portion of ethyl acetate. The combined organic layer was dried over anhydrous Na$_2$CO$_3$, and concentrated. The crude product was purified by chromatography on a silica gel column. Elution with 9:1 hexanes-ethyl acetate afforded compound 2 as pale yellow solid: yield 1.98 g (71%); silica gel TLC $R_f$ 0.37 (4:1 hexanes/ethyl acetate); $^1$H NMR (400 MHz, CDCl$_3$) δ 1.01 (s, 6H), 2.03 (s, 3H), 2.18 (s, 2H), 2.51 (s, 2H) and 6.62 (s, 1H); $^{13}$C NMR (100 MHz, CDCl$_3$) δ 25.3, 27.8, 32.4, 42.6, 45.6, 78.2, 112.4, 113.2, 120.5, 159.9 and 170.4. ESI MS (m/z): 186.1 (M$^+$)

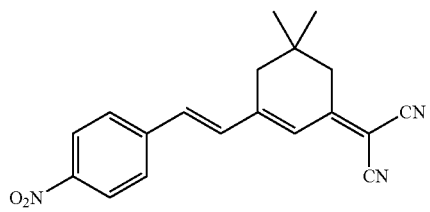

(E)-2-(5,5-dimethyl-3-(4-nitrostyryl) cyclohex-2-en-1-ylidene) malononitrile (3): To a stirred solution of 1.92 g (10.3 mmol) of compound 2, 0.15 mL of piperidine in 40 mL of acetonitrile was added 4-nitrobenzaldehyde (2.34 g, 15.5 mmol). The reaction mixture was stirred at 50° C. for 6 h. After the reaction mixture was allowed to cool to room temperature, the formed precipitate was filtered, washed with acetonitrile, and recrystallized with ethanol to obtained compound 3 as yellow crystal: yield 2.96 g (90%); $^1$H NMR (400 MHz, CDCl$_3$) δ 1.11 (s, 6H), 2.50 (s, 2H), 2.64 (s, 2H), 6.94 (s, 1H), 7.06 (d, 1H, J=16.1 Hz), 7.13 (d, 1H, J=16.2 Hz), 7.66 (d, 2H, J=8.8 Hz) and 8.25 (d, 2H, J=8.7 Hz); $^{13}$C NMR (100 MHz, CDCl$_3$) δ 28.0, 32.0, 39.1, 42.9, 80.7, 112.3, 113.0, 124.3, 125.6, 127.9, 133.2, 133.7, 141.9, 147.9, 152.2 and 168.8. ESI MS (m/z): 319.2 (M$^+$)

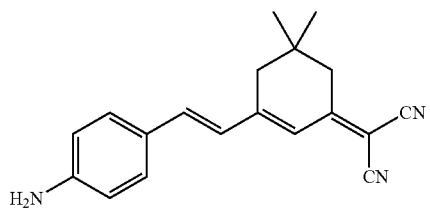 [SMILES: CC1(C)CC(/C=C/c2ccc([N+](=O)[O-])cc2)=CC(=C(C#N)C#N)C1]

(E)-2-(3-(4-aminostyryl)-5,5-dimethylcyclohex-2-en-1-ylidene) malononitrile (4): To a stirred solution of 2.60 g (8.14 mmol) of compound 3 and 2.32 g (12.2 mmol) of SnCl$_2$ in 50 mL of ethyl acetate was added 0.5 mL of hydrochloric acid dropwise. The reaction mixture was refluxed for 8 h. After, the solvent was evaporated under reduced pressure, the obtained residue was washed with 15% sodium hydroxide solution and extracted with three 50 mL portions of ethyl acetate. The combined organic layer was dried over anhydrous Na$_2$SO$_4$, and concentrated. The resulted crude product was further purified by chromatography on a silica gel column. Elution with 4:1 hexanes-ethyl acetate afford compound 4 as red powder: yield 2.07 g (88%); silica gel TLC $R_f$ 0.18 (7:3 hexanes/ethyl acetate); $^1$H NMR (400 MHz, CDCl$_3$) δ 1.07 (s, 6H), 2.44 (s, 2H), 2.58 (s, 2H), 3.99 (brs, 2H), 6.67 (d, 2H, J=8.5 Hz), 6.76 (s, 1H), 6.81 (d, 1H, J=16.0 Hz), 7.00 (d, 1H, J=16.0 Hz) and 7.34 (d, 2H, J=8.4 Hz); $^{13}$C NMR (100 MHz, CDCl$_3$) δ 28.0, 32.0, 39.2, 43.0, 113.2, 114.0, 115.1, 121.9, 125.3, 126.0, 129.5, 137.7, 148.4, 154.9 and 169.3. ESI MS (m/z): 288.1 (M-1)

Synthesis of NIR-ASM: NIR-ASM was synthesized by coupling (E)-2-(3-(4-aminostyryl)-5,5-dimethylcyclohex-2-en-1-ylidene) malononitrile (4, ASM) and 3-methyl-3-(2,4,5-trimethyl-3,6-dioxocyclohexa-1,4-dien-1-yl) butanoic acid (7, QPA) using 1-Ethyl-3-(3-dimethylaminopropyl) carbodiimide (EDC).

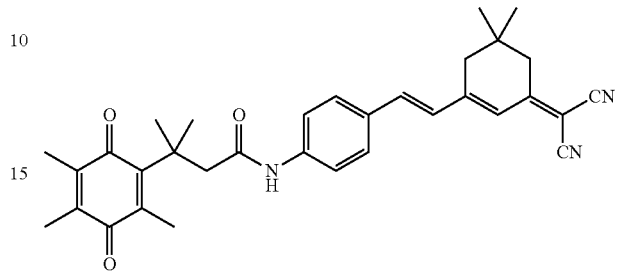

(E)-N-(4-(2-(3-(dicyanomethylene)-5,5-dimethylcyclohex-1-en-1-yl)vinyl)phenyl)-3-methyl-3-(2,4,5-trimethyl-3,6-dioxocyclohexa-1,4-dien-1-yl)butanamide (NIR-ASM): To a stirred solution of 250 mg (1.00 mmol) of compound 7 in 1 mL of dry pyridine was added 287 mg (1.50 mmol) of EDC at room temperature. After 20 min a solution of 289 mg (1.00 mmol) of compound 4 in 0.2 mL of pyridine was added to the reaction mixture and stirred for 10 h at room temperature. The reaction mixture was diluted with 50 mL of 1N HCl and extracted with two 30 mL portions of ethyl acetate. Combined organic layer was dried over Na$_2$SO$_4$ and concentrated under diminished pressure. The obtained crude product was purified by chromatography on a silica gel column. Elution with 4:1 hexanes-ethyl acetate afforded compound NIR-ASM as yellow solid: yield 427 mg (82%); silica gel TLC $R_f$ 0.19 (7:3 hexanes/ethyl acetate); 1H NMR (400 MHz, CDCl$_3$) δ 1.07 (s, 6H), 1.50 (s, 6H), 1.95 (s, 3H), 1.96 (s, 3H), 2.16 (s, 3H), 2.45 (s, 2H), 2.59 (s, 2H), 3.06 (s, 2H), 6.81 (s, 1H), 6.89 (d, 1H, J=16.1 Hz), 6.99 (d, 1H, J=16.1 Hz), 7.34 (s, 1H), 7.43 (d, 2H, J=8.8 Hz) and 7.47 (d, 2H, J=8.7 Hz); 13C NMR (100 MHz, CDCl$_3$) δ 12.2, 12.7, 14.2, 28.0, 29.1, 32.0, 38.4, 39.2, 43.0, 50.5, 78.3, 112.8, 113.6, 119.8, 123.3, 128.2, 128.4, 131.5, 136.4, 138.4, 138.5, 139.0, 143.2, 152.7, 154.0, 169.3, 170.4, 187.5 and 191.5. ESI MS (m/z): 521.3 (M-1).

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES—BACKGROUND AND EXAMPLE 1

1. Eranster, L.; Navazio, F. Soluble diaphorase in animal tissues. Acta Chem. Scand. 1958, 12, 595-602.
2. Li, R.; Bianchet, M. A.; Talalay, P.; Amzel, L. M. The threedimensional structure of NAD(P)H:quinone reductase, a flavoprotein involved in cancer chemoprotection and chemotherapy: Mechanism of the two-electron reduction. Proc. Natl. Acad. Sci. USA 1995, 92, 8846-8850.
3. Dinkova-Kostova, A. T.; Talalay, P. NAD(P)H:quinone acceptor oxidoreductase 1 (NQO1), a multifunctional antioxidant enzyme and exceptionally versatile cytoprotector. Arch. Biochem. Biophys. 2010, 501, 116-123.
4. Yang, Y.; Zhang, Y.; Wu, Q.; Cui, X.; Lin, Z.; Liu, S.; Chen, L. Clinical implications of high NQO1 expression in breast cancers. J. Exp. Clin. Cancer Res. 2014, 33, 14, doi: 10.1186/1756-9966-33-14.
5. Cui, X.; Jin, T.; Wang, X.; Jin, G.; Li, Z.; Lin, L. NAD(P)H: Quinone oxidoreductase-1 overexpression predicts poor prognosis in small cell lung cancer. Oncol. Rep. 2014, 32, 2589-2595.
6. Li, Z.; Zhang, Y.; Jin, T.; Men, J.; Lin, Z.; Qi, P.; Piao, Y.; Yan, G. NQO1 protein expression predicts poor prognosis of non-small cell lung cancers. BMC Cancer 2015, 15, 207, doi: 10.1186/s12885-015-1227-8.
7. Dong, Y.; Bey, E. A.; Li, L. S.; Kabbani, W.; Yan, J.; Xie, X. J.; Hsieh, J. T.; Gao, J.; Boothman, D. A. Prostate cancer radiosensitization through PARP-1 hyperactivation. Cancer Res. 2010, 70, 8088-8096.
8. Lin, L.; Qin, Y.; Jin, T.; Liu, S.; Zhang, S.; Shen, X.; Lin, Z. Significance of NQO1 overexpression for prognostic evaluation of gastric adenocarcinoma. Exp. Mol. Pathol. 2014, 96, 200-205.
9. Ji, L.; Wei, Y.; Jiang, T.; Wang, S. Correlation of Nrf2, NQO1, MRP1, cmyc and p53 in colorectal cancer and their relationships to clinicopathologic features and survival. Int. J. Clin. Exp. Pathol. 2014, 7, 1124-1131.
10. Lewis, A. M.; Ough, M.; Du, J.; Tsao, M. S.; Oberley, L. W.; Cullen, J. J. Targeting NAD(P)H:Quinone Oxi- 10. doreductase (NQO1) in Pancreatic Cancer. Mol. Carcinog. 2017, 56, 1825-1834.
11. Okamura, T.; Kurisu, K.; Yamamoto, W.; Takano, H.; Nishiyama, M. NADPH/quinone oxidoreductase is a priority target of glioblastoma chemotherapy. Int. J. Oncol. 2000, 16, 295-598.
12. Li, L. S.; Reddy, S.; Lin, Z. H.; Liu, S.; Park, H.; Chun, S. G.; Bornmann, W. G.; Thibodeaux, J.; Yan, J.; Chakrabarti, G.; et al. NQO1-Mediated Tumor-Selective Lethality and Radiosensitization for Head and Neck Cancer. Mol. Cancer Ther. 2016, 15, 1757-1767.
13. Zhang, K.; Chen, D.; Ma, K.; Wu, X.; Hao, H.; Jiang, S. NAD(P)H:Quinone Oxidoreductase 1 (NQO1) as a Therapeutic and Diagnostic Target in Cancer. J. Med. Chem. 2018, 61, 6983-7003.
14. Leinonen, H. M.; Kansanen, E.; Polonen, P.; Heinaniemi, M.; Levonen, A. L. Role of the Keap1-Nrf2 pathway in cancer. Adv. Cancer Res. 2014, 122, 281-320.
15. Nioi, P.; McMahon, M.; Itoh, K.; Yamamoto, M.; Hayes, J. D. Identification of a novel Nrf2-regulated antioxidant response element (ARE) in the mouse NAD(P)H:quinone oxidoreductase 1 gene: Reassessment of the ARE consensus sequence. Biochem. J. 2003, 374, 337-348.
16. Tonelli, C.; Chio, I. I. C.; Tuveson, D. A. Transcriptional Regulation by Nrf2. Antioxid Redox Signal. 2018, 29, 1727-1745.
17. Belykh, E.; Martirosyan, N. L.; Yagmurlu, K.; Miller, E. J.; Eschbacher, J. M.; Izadyyazdanabadi, M.; Bardonova, L. A.; Byvaltsev, V. A.; Nakaji, P.; Preul, M. C. Intraoperative Fluorescence Imaging for Personalized Brain Tumor Resection: Current State and Future Directions. Front. Surg. 2016, 3, 55.
18. Stummer, W.; Reulen, H. J.; Meinel, T.; Pichlmeier, U.; Schumacher, W.; Tonn, J. C.; Rohde, V.; Oppel, F.; Turowski, B.; Woiciechowsky, C.; et al. Extent of resection and survival in glioblastoma multiforme: Identification of and adjustment for bias. Neurosurgery 2008, 62, 564-576.
19. Zhang, D. Y.; Singhal, S.; Lee, J. Y. K. Optical Principles of Fluorescence-Guided Brain Tumor Surgery: A Practical Primer for the Neurosurgeon. Neurosurgery 2018, doi:10.1093/neuros/nyy315.
20. Swanson, K. I.; Clark, P. A.; Zhang, R. R.; Kandela, L K.; Farhoud, M.; Weichert, J. P.; Kuo, J. S. Fluorescent Cancer-Selective Alkylphosphocholine Analogs for Intraoperative Glioma Detection, Neurosurgery 2015, 76, 115-124.
21. Lee, S.; Xie, J.; Chen, X. Activatable molecular probes for cancer imaging. Curr. Top. Med. Chem. 2010, 10, 1135-1144.
22. Wirth, D.; Snuderl, M.; Sheth, S.; Kwon, C. S.; Frosch, M. P.; Curry, W.; Yaroslaysky, A. N. Identifying brain neoplasms using dye-enhanced multimodal confocal imaging. J. Biomed Opt. 2012, 17, 026012, doi: 10.1117/1.JBO.17.2.026012.
23. Dias, G. G.; King, A.; de Moliner, M.; Vendrell, M.; da Siva Junior, E. N. Quinone based fluorophores for imaging biological processes. Chem. Soc. Rev. 2018, 47, 12-27.
24. Mendoza, M. F.; Hollabaugh, N. M.; Hettiarachchi, S. U.; McCarley, R. L. Human NAD(P)H:Quinone Oxidoreductase Type I (hNQO1) Activation of Quinone Propionic Acid Trigger Groups. Biochemistry, 2012, 51, 8014-8026.
25. Silvers, W. C.; Payne, A. S.; McCarley, R. L. Shedding light by cancer redox-human NAD(P)H: Quinone oxidoreductase 1 activation of a cloaked fluorescent dye. Chem. Commun. 2011, 47, 11264-11266.
26. Best, Q. A.; Johnson, A. E.; Prasai, B.; Rouillere, A.; McCarley, R. L. Environmentally Robust Rhodamine Reporters for Probe-based Cellular Detection of the Cancer-linked Oxidoreductase hNQO1. ACS Chem. Biol. 2016, 11, 231-240.
27. Hettiarachchi, S. U.; Prasai, B.; McCarley, R. L. Detection and Cellular Imaging of Human Cancer Enzyme Using a Turn-On, Wavelength-Shiftable, Self-Immolative Profluorophore. J. Am. Chem. Soc. 2014, 136, 7575-7578.
28. Prasai, B.; Silvers, W. C.; McCarley, R. L. Oxidoreductase-Facilitated Visualization and Detection of Human Cancer Cells. Anal. Chem. 2015, 87, 6411-6418.
29. Pan, D.; Luo, F.; Liu, X.; Liu, W.; Chen, W.; Liu, F.; Kuang, Y. Q.; Jiang, J. H. A novel two-photon fluorescent probe with a long Stokes shift and a high signal-to background ratio for human NAD(P)H:quinone oxidoreductase 1 (hNQO1) detection and imaging in living cells and tissues. Analyst 2017, 142, 2624-2630.
30. Cuff, S.; Lewis, R. D.; Chinje, E.; Jaffar, M.; Knox, R.; Weeks, I. An improved cell-permeable fluorogenic substrate as the basis for a highly sensitive test for NAD(P)H quinone oxidoreductase 1 (NQO1) in living cells. Free Radic. Biol. Med. 2018, 116, 141-148.
31. Fei, Q.; Zhou, L.; Wang, F.; Shi, B.; Li, C.; Wang, R.; Zhao, C. Rational construction of probes rendering ratiometric response to the cancer-specific enzyme NQO1. Dyes Pigm. 2017, 136, 846-851.
32. Shin, W. S.; Lee, M. G.; Verwilst, P.; Lee, J. H.; Chi, S. G.; Kim, J. S. Mitochondria-targeted aggregation induced emission theranostics: Crucial importance of in situ activation. Chem. Sci. 2016, 7, 6050-6059.
33. Kwon, N.; Cho, M. K.; Park, S. J.; Kim, D.; Nam, S. J.; Cui, L.; Kim, H. M.; Yoon, J. An efficient two-photon fluorescent probe for human NAD(P)H:quinone oxidoreductase (hNQO1) detection and imaging in tumor cells. Chem. Commun. 2017, 53, 525-528.
34. Shen, Z.; Prasai, B.; Nakamura, Y.; Kobayashi, H.; Jackson, M. S.; McCarley, R. L. A Near-Infrared, Wavelength-Shiftable, Turn-on Fluorescent Probe for the Detection and Imaging of Cancer Tumor Cells. ACS Chem. Biol. 2017, 12, 1121-1132.
35. Zhang, C.; Zhai, B. B.; Peng, T.; Zhong, Z.; Xu, L.; Zhang, Q. Z.; Li, L. Y.; Yi, L.; Xi, Z. Design and synthesis of near-infrared fluorescence enhancement probes for the cancer-specific enzyme hNQO1. Dyes and Pigm. 2017, 143, 245-251.
36. Gontijo, T. B.; de Freitas, R. P.; de Lima, G. F.; de Rezende, L. C.; Pedrosa, L. F.; Silva, T. L. F.; Goulart, M. O.; Cavalcanti, B. C.; Pessoa, C.; Bruno, M. P.; et al. Novel fluorescent lapachone based BODIPY: Synthesis, computational and electrochemical aspects, and subcellular localisation of a potent antitumour hybrid quinone. Chem. Commun. 2016, 2, 13281-13284.
37. Gontijo, T. B.; de Freitas, R. P.; Emery, F. S.; Pedrosa, L. F.; Vieira Neto, J. B.; Cavalcanti, B. C.; Pessoa, C.; King, A.; de Moliner, F.; Vendrell, M.; da Silva Júnior, E. N. On the synthesis of quinone based BODIPY hybrids: New insights on antitumor activity and mechanism of action in cancer cells. Bioorg. Med. Chem. Lett. 2017, 27, 4446-4456.
38. Bian, J.; Li, X.; Xu, L.; Wang, N.; Qian, X.; You, Q.; Zhang, X. Affinity-based small fluorescent probe for NAD(P)H:quinone oxidoreductase 1 (NQO1). Design, synthesis and pharmacological evaluation. Eur. J. Med. Chem. 2017, 127, 828-839.
39. Winski, S. L.; Faig, M.; Bianchet, M. A.; Siegel, D.; Swann, E.; Fung, K.; Duncan, M. W.; Moody, C. J.; Amzel, L. M.; Ross, D. Characterization of a Mechanism Based Inhibitor of NAD(P)H:Quinone Oxidoreductase 1 by Biochemical, X-ray Crystallographic, and Mass Spectrometric Approaches. Biochemistry 2001, 40, 15135-15142.
40. Punganuru, S. R.; Madala, H. R.; Mikelis, C. M.; Dixit, A.; Arutla, V.; Srivenugopal, K. S. Conception, synthesis, and characterization of a rofecoxib-combretastatin hybrid drug with potent cyclooxygenase-2 (COX-2) inhibiting and microtubule disrupting activities in colon cancer cell culture and xenograft models. Oncotarget 2018, 9, 26109-26129.
41. Fang, J.; Nakamura, H.; Maeda, H. The EPR effect: Unique features of tumor blood vessels for drug delivery, factors involved, and limitations and augmentation of the effect. Adv. Drug Deliv. Rev. 2011, 63, 136-151.
42. Madala, H. R.; Punganuru, S. R.; Ali-Osman, F.; Zhang, R.; Srivenugopal, K. S. Brain- and brain tumor-penetrating disulfiram nanoparticles: Sequence of cytotoxic events and efficacy in human glioma cell lines and intracranial xenografts. Oncotarget 2017, 9, 3459-3482.

REFERENCES—EXAMPLE 2

(1) Fass, L. Imaging and cancer: a review. Mol. Oncol. 2, 115-152 (2008).
(2) Liu, B. et al. Gastrointestinal imaging-practical magnetic resonance imaging approach. World J. Radiol. 6, 544-566 (2016).
(3) Frangioni, J. V. New technologies for human cancer imaging. J. Clin. Oncol. 26, 4012-4021 (2008).
(4) Prince, A. C. et al. Characterizing the detection threshold for optical imaging in surgical oncology. J. Surg Oncol. 116, 898-906 (2017).
(5) Lacivita, E., Leopoldo, M., Berardi, F., Colabufo, N. A. & Perrone, R. Activatable fluorescent probes: A new concept in optical molecular imaging. Curr. Med. Chem. 19, 4731-4741 (2012).
(6) Garland, M., Yim, J. J. & Bogyo, M. A bright future for precision medicine: Advances in fluorescent chemical probe design and their clinical application. Cell Chem. Biol. 23, 122-136 (2016).
(7) Luo, S. et al. A Probe for the Detection of Hypoxic Cancer Cells. ACS Sens. 2, 1139-1145 (2017).
(8) Okuda, K. et al. 2-Nitroimidazole-Tricarbocyanine Conjugate as a Near-Infrared Fluorescent Probe for in Vivo Imaging of Tumor Hypoxia. Bioconjugate Chem. 23, 324-329 (2012).
(9) Parkinson, E. I. & Hergenrother, P. J. Deoxynyboquinones as NQO1-activated cancer therapeutics. Acc. Chem. Res. 48, 2715-2723 (2015).
(10) Oh, E. T. & Park, H. J. Implications of NQO1 in cancer therapy. BMB Rep. 48, 609-617 (2015).
(11) Gaikwad, A., Long, D. J., Stringer, J. L. & Jaiswal, A. K. In vivo role of NAD(P)H: Quinone Oxidoreductase 1 (NQO1) in the regulation of intracellular redox state and accumulation of abdominal adipose tissue. J. Biol. Chem. 276, 22559-22564 (2001).
(12) Yang, Y. et al. Clinical implications of high NQO1 expression in breast cancers. J. Exp. Clin. Cancer Res. 33, 14 (2014).
(13) Cui, X. et al. NAD(P)H: quinone oxidoreductase-1 overexpression predicts poor prognosis in small cell lung cancer. Oncol. Rep. 32, 2589-2595 (2014).
(14) Li, Z. et al. BMC Cancer 15, 207 (2015).
(15) Dong, Y. et al. Prostate cancer radiosensitization through poly(ADP-ribose) polymerase-1 hyperactivation. Cancer Res. 70, 8088-8096 (2010).
(16) Lin, L. et al. Significance of NQO1 overexpression for prognostic evaluation of gastric adenocarcinoma. Exp. Mol. Pathol. 96, 200-205 (2014).
(17) Ji, L., Wei, Y., Jiang, T. & Wang, S. Correlation of Nrf2, NQO1, MRP1, cmyc and p53 in colorectal cancer and their relationships to clinicopathologic features and survival. Int. J. Clin. Exp. Pathol. 7, 1124-1131 (2014).
(18) Lewis, A. M. et al. Targeting NAD(P)H: quinone oxidoreductase (NQO1) in pancreatic cancer. J. Mol. Carcinog. 56, 1825-1834 (2017).
(19) Li, L. S. et al. NQO1-Dependent radiosensitization of head and neck cancer. Mol. Cancer Ther. 15, 1757-1767 (2016).
(20) Dias, G. G., King, A., de Moliner, M., Vendrell, M. & da Siva Junior, E. N. Quinone-based fluorophores for imaging biological processes. Chem. Soc. Rev. 47, 12-27 (2018).
(21) Mendoza, M. F., Hollabaugh, N. M., Hettiarachchi, S. U. & McCarley, R. L. Human NAD(P)H:quinone oxidoreductase type I (hNQO1) activation of quinone propionic acid trigger groups. Biochemistry, 51, 8014-8026 (2012).
(22) Silvers, W. C., Payne, A. S. & McCarley, R. L. Shedding light by cancer redox-human NAD(P)H:quinone oxidoreductase 1 activation of a cloaked fluorescent dye. Chem. Commun. 47, 11264-11266 (2011).
(23) Best, Q. A., Johnson, A. E., Prasai, B., Rouillere, A. & McCarley, R. L. Environmentally robust rhodamine reporters for probe-based cellular detection of the cancer-linked oxidoreductase hNQO1. ACS Chem. Biol. 11, 231-240 (2016).
(24) Silvers, W. C., Prasai, B., Burk, D. H., Brown, M. L. & McCarley, R. L. Profluorogenic reductase substrate for rapid, selective, and sensitive visualization and detection of human cancer cells that overexpress NQO1. J. Am. Chem. Soc. 135, 309-314 (2013).
(25) Hettiarachchi, S. U., Prasai, B. & McCarley, R. L. Detection and cellular imaging of human cancer enzyme using a turn-on, wavelength-shiftable, self-immolative profluorophore. J. Am. Chem. Soc. 136, 7575-7578 (2014).
(26) Prasai, B., Silvers, W. C. & McCarley, R. L. Oxidoreductase-facilitated visualization and detection of human cancer cells. Anal. Chem. 87, 6411-6418 (2015).
(27) Pan, D. et al. A novel two-photon fluorescent probe with a long Stokes shift and a high signal-to-background ratio for human NAD(P)H:quinone oxidoreductase 1 (hNQO1) detection and imaging in living cells and tissues. Analyst, 142, 2624-2630 (2017).
(28) Cuff, S. et al. An improved cell-permeable fluorogenic substrate as the basis for a highly sensitive test for NAD(P)H quinone oxidoreductase 1 (NQO1) in living cells. Free Radic. Biol. Med. 116, 141-148 (2018).
(29) Fei, Q. et al. Rational construction of probes rendering ratiometric response to the cancer-specific enzyme NQO1. Dyes Pigm. 136, 846-851 (2017).
(30) Shin, W. S. et al. Mitochondria-targeted aggregation induced emission theranostics: crucial importance of in situ activation. Chem. Sci. 7, 6050-6059 (2016).

(31) Kwon, N. et al. An efficient two-photon fluorescent probe for human NAD(P)H:quinone oxidoreductase (hNQO1) detection and imaging in tumor cells. Chem. Commun. 53, 525-528 (2017).
(32) Shen, Z. et al. A near-infrared, wavelength-shiftable, turn-on fluorescent probe for the detection and imaging of cancer tumor cells. ACS Chem. Biol. 12, 1121-1132 (2017).
(33) Zhang, C. et al. Design and synthesis of near-infrared fluorescence-enhancement probes for the cancer-specific enzyme hNQO1. Dyes Pigm. 143, 245-251 (2017).
(34) Gontijo, T. B. et al. Novel fluorescent lapachone-based BODIPY: synthesis, computational and electrochemical aspects, and subcellular localization of a potent antitumour hybrid quinone. Chem. Commun. 52, 13281-13284 (2016).
(35) Gontijo, T. B. et al. On the synthesis of quinone-based BODIPY hybrids: New insights on antitumor activity and mechanism of action in cancer cells. Bioorg. Med. Chem. Lett. 27, 4446-4456 (2017).
(36) Bian, J. et al. Affinity-based small fluorescent probe for NAD(P)H:quinone oxidoreductase 1 (NQO1). Design, synthesis and pharmacological evaluation. Eur. J. Med. Chem. 127, 828-839 (2017).
(37) Punganuru, S. R. et al. Cancer-Specific Biomarker hNQO1-Activatable Fluorescent Probe for Imaging Cancer Cells In Vitro and In Vivo. Cancers (Basel) 10, E470 (2018).
(38) Zhang, X., Bloch, S., Akers, W. & Achilefu, S. Curr. Protoc. Cytom. John Wiley & sons, Inc (2012).
(39) Luo, S., Zhang, E., Su, Y., Cheng, T. & Shi, C. A review of NIR dyes in cancer targeting and imaging. Biomaterials, 32, 7127-7138 (2011).
(40) (a) Zhang, W. et al. Near-infrared fluorescent probe with remarkable large stokes shift and favorable water solubility for real-time tracking leucine aminopeptidase in living cells and in vivo. Anal Chem. 89, 12319-12326 (2017).
(41) Ghoroghchian, P. P., Therien, M. J. & Hammer, D. A. Wiley Interdiscip. Rev. Nanomed. Nanobiotechnol. John Wiley & Sons, Inc (2011).
(42) Winski, S. L. et al. Characterization of a mechanism-based inhibitor of NAD(P)H:quinone oxidoreductase 1 by biochemical, X-ray crystallographic, and mass spectrometric approaches. Biochemistry, 40, 15135-15142 (2001).
(43) Punganuru, S. R. et al. Design and synthesis of a C7-aryl piperlongumine derivative with potent antimicrotubule and mutant p53-reactivating properties. Eur. J. Med. Chem. 107, 233-244 (2016).
(44) Kellar, A., Egan, C. & Morris, D. Biomed. Res. Int. 621324 org/10.1155/2015/621324 (2015).
(45) Huang, X. et al. An NQO1 substrate with potent antitumor activity that selectively kills by PARP1-induced programmed necrosis. Cancer Res. 72, 3038-3047 (2012).

What is claimed is:

1. An assay to detect human NAD(P)H quinone oxidoreductase-1 (hNQO1) enzyme activity comprising:
   contacting an hNQO1 enzyme with a probe comprising a quinone propionic acid (QPA) conjugated to dicyanoisophorone (DCP), wherein the hNQO1 reduces the probe and releases a fluorescent DCP.

2. The assay of claim 1, wherein the probe is defined as further comprising an ester or amide bond between the QPA and the DCP.

3. The assay of claim 1, wherein the probe has at least one of: a large stokes shift, a sensitivity and selectivity against hNQO1, no cytotoxicity up to 100 µM, or cell permeability.

4. The assay of claim 1, the probe has the formula:

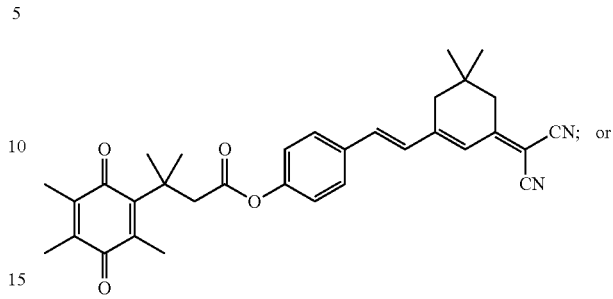

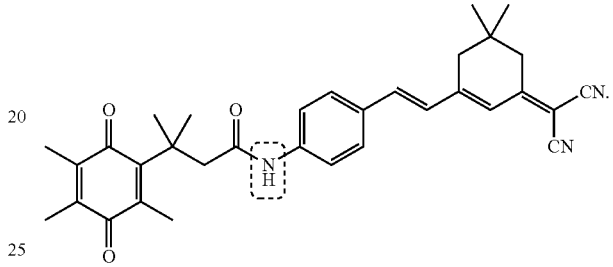

5. The assay of claim 1, wherein a redox activity of hNQO1 reduces a quinone moiety of QPA into an o-hydroxydihydrocinnamic acid derivative that undergoes lactonization under physiological conditions to yield dihydrocoumarin and fluorescent DCP.

6. The assay of claim 1, wherein the hNQO1 enzyme is in a cell, a tissue, an organ, or a cancer.

7. The assay of claim 1, wherein the hNQO1 enzyme is in a breast, lung, prostate, stomach, colon, pancreatic, brain, or head and neck cancer.

8. A probe comprising a quinone propionic acid (QPA) conjugated to a dicyanoisophorone (DCP).

9. The probe of claim 8, wherein the quinone propionic acid (QPA) is conjugated to the dicyanoisophorone (DCP) by an ester or amide bond.

10. The probe of claim 8, wherein the probe has the formula:

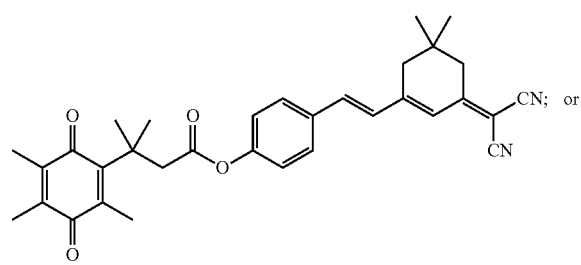

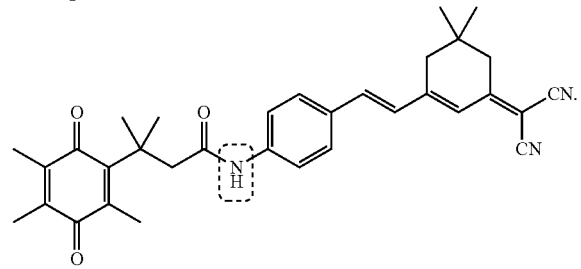

11. The probe of claim 8, wherein the probe has at least one of: a large stokes shift, a sensitivity and selectivity against hNQO1, no cytotoxicity up to 100 μM, or cell permeability.

12. The probe of claim 8, wherein the probe is reduced by a human NAD(P)H quinone oxidoreductase-1 (hNQO1) enzyme.

13. The probe of claim 8, wherein the probe is a dicyanoisophorone (DCP) fluorophore conjugated to a NQO1 substrate quinone propionic acid (QPA).

14. The probe of claim 8, wherein a redox activity of hNQO1 reduces a quinone moiety of QPA into an o-hydroxydihydrocinnamic acid derivative that undergoes lactonization under physiological conditions to yield dihydrocoumarin and fluorescent DCP.

15. The probe of claim 8, wherein the hNQO1 enzyme is in a cell, a tissue, an organ, or a cancer.

16. The probe of claim 8, wherein the hNQO1 enzyme is in a breast, lung, prostate, stomach, colon, pancreatic, brain, or head and neck cancer.

17. A method of detecting a cancer cell that expresses a human NAD(P)H quinone oxidoreductase-1 (hNQO1) enzyme comprising:
    contacting the cancer cell with a probe comprising a quinone propionic acid (QPA) conjugated to dicyanoisophorone (DCP), wherein the hNQO1 reduces the probe and releases a fluorescent DCP; and detecting fluorescence in the cancer cell.

18. The method of claim 17, wherein the quinone propionic acid (QPA) is conjugated to the dicyanoisophorone (DCP) by an ester or amide bond.

19. The method of claim 17, wherein the quinone propionic acid (QPA) conjugated to dicyanoisophorone (DCP) has the formula:

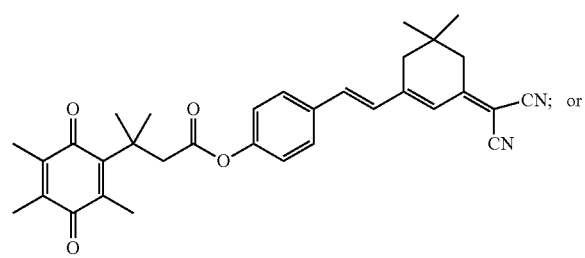

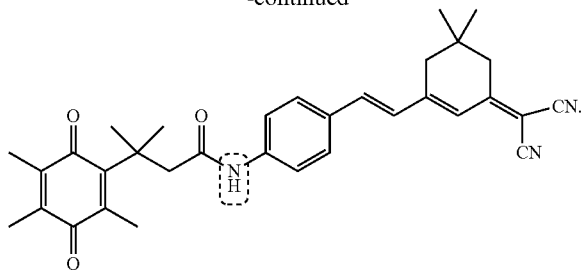

20. The method of claim 17, wherein the probe has at least one of: a large stokes shift, a sensitivity and selectivity against hNQO1, no cytotoxicity up to 100 μM, or cell permeability.

21. The method of claim 17, wherein a redox activity of hNQO1 reduces a quinone moiety of QPA into an o-hydroxydihydrocinnamic acid derivative that undergoes lactonization under physiological conditions to yield dihydrocoumarin and fluorescent DCP.

22. The method of claim 17, wherein the fluorescence is detected in vivo.

23. The method of claim 17, further comprising the step of obtaining a sample from a subject and measuring the activity of the hNQO1 in the sample.

24. The method of claim 17, wherein the cancer is a breast, lung, prostate, stomach, colon, pancreatic, brain, or head and neck cancer.

25. A method of making a probe comprising a quinone propionic acid (QPA) conjugated to dicyanoisophorone (DCP) comprising:
    carrying out the following reaction:

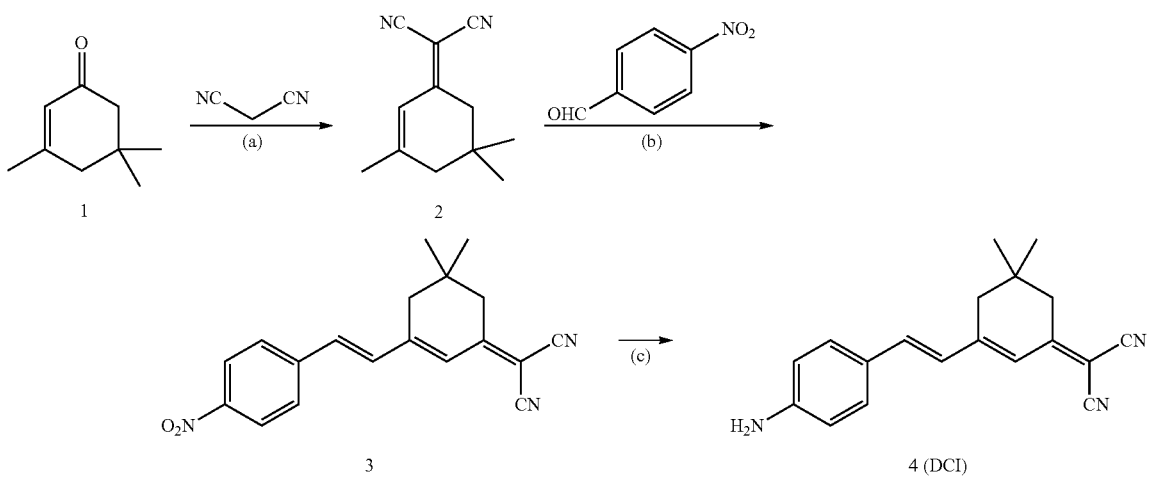

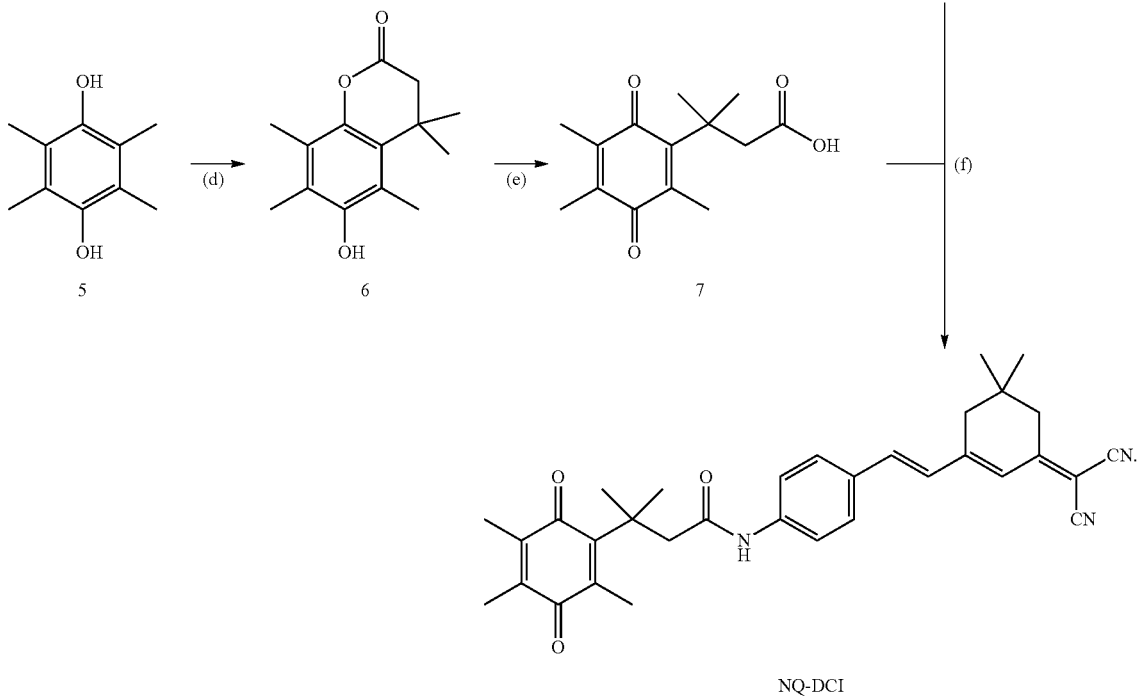
wherein the conditions are:
(a) ammonium acetate, acetic anhydride, acetic acid, toluene, reflux, 12 h;
(b) piperidine, acetonitrile, 50° C., 6 h;
(c) SnCl$_2$, HCl, ethyl acetate, 8 h;
(d) methyl 3,3-dimethylacrylate, methanesulfonic acid, 70° C., 2 h;
(e) N-Bromosuccinimide, acetonitrile, water, room temperature, 1 h; and
(f) 1-Ethyl-3-(3-dimethylaminopropyl)carbodiimide, pyridine, rt, 10 h.
* * * * *